(12) United States Patent
Xiao et al.

(10) Patent No.: US 6,593,099 B2
(45) Date of Patent: Jul. 15, 2003

(54) REGULATION OF HUMAN S-ACYL FATTY ACID SYNTHASE THIOESTERASE-LIKE ENZYME

(75) Inventors: Yonghong Xiao, Cambridge, MA (US); Eric Marshall Towler, New Haven, CT (US); Jamie Frederick Eveleigh, West Haven, CT (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/888,623

(22) Filed: Jun. 26, 2001

(65) Prior Publication Data

US 2002/0042115 A1 Apr. 11, 2002

Related U.S. Application Data

(60) Provisional application No. 60/214,012, filed on Jun. 26, 2000, and provisional application No. 60/255,148, filed on Dec. 14, 2000.

(51) Int. Cl.[7] .................................................. C12Q 1/44
(52) U.S. Cl. ........................... 435/19; 435/18; 435/197; 536/23.2
(58) Field of Search ................................ 536/23.2, 23.5; 435/19, 18, 196, 197

(56) References Cited

U.S. PATENT DOCUMENTS 5,147,792 A    9/1992   Perchorowicz et al. ..... 435/134

FOREIGN PATENT DOCUMENTS

EP    1 074 617 A    2/2001

OTHER PUBLICATIONS

Safford et al. "Molecular cloning and sequence analysis of complementary DNA . . . " Biochemistry 1987, 26, 1358–1364.*

Isogai et al. Data Base GenEmbl, Accession No. AK001844.*

Seffernick et al. "Melamine Deaminase and Atrazine Chlorohydrolase: 98 Percent Identical but Functionally Different" J. Bacteriol. Apr. 2001, 2405–2410.*

R. Strausberg, Accession No. Al125696, "qd95a09.×1 Soares_testis_NHT *Homo sapiens* cDCNA clone IMAGE: 1737208, s–acyl fatty acid synthase thioesterase," Database EMBL 'Online! EBl, Sep. 22, 1998.

ISOGAI, Accession No. AK001968, "*Homo sapiens* cDNA FLJ11106 fis, clone place 1005763, s–acyl fatty acid synthase thioesterase", Database EMBL 'Online! EBI, Feb. 22, 2000.

Cater, et al., "Serum Low–Density Lipoprotein Cholesterol Response to Modification of Saturated Fat Intake: Recent Insights", Current Opinion in Lipidology, 1997, pp. 332–336, V.896, Rapid Science Publishers, USA.

Dehesh, et al., "Production of High Levels of 8:0 and 10:0 Fatty Acids in Transgenic Canola by Overexpression of Ch FatB2, a thioesterase cDNA from *Cuphea hookeriana*", Plant Journal, 1996, pp. 167–172, V.9 (2), Blackwell Scientific and Bios Scientific Publishers, USA.

Libertini, et al., "Purification and Properties of a Thioesterase from Lactating Rat Mammary Gland Which Modifies the Product Specificity of Fatty Acid Synthetase", Journal of Biological Chemistry, 1978, pp. 1393–1401, V.253 (5), American Society of Biological Chemists, USA.

Mensink, et al., "Dietary Saturated and Trans Fatty Acids and Lipoprotein Metabolism", Annales of Medicine, 1994, pp. 461–464, V.26 (6), Blackwell Science, USA.

Tsai, et al., "Mechanisms Mediating Lipoprotein Responses to Diets with Medium–Chain Triglyceride and Lauric Acid", Lipids, 1999, pp. 895–904V.34 (9), The American Oil Chemist's Society Press, USA.

Witkowska, et al., "The Carboxyl–terminal Region of Thioesterase II Participates in the Interaction with Fatty Acid Synthase", Journal of Biological Chemistry, 1990, pp. 5662–5665, V.265 (10), American Society of Biological Chemists, USA.

* cited by examiner

Primary Examiner—Nashaat T. Nashed
(74) Attorney, Agent, or Firm—Banner & Witcoff, Ltd.

(57) ABSTRACT

Reagents which regulate human S-acyl fatty acid synthase thioesterase-like enzyme and reagents which bind to human S-acyl fatty acid synthase thioesterase-like enzyme gene products can play a role in preventing, ameliorating, or correcting dysfunctions or diseases including, but not limited to cardiovascular disease, hyperlipidemia, obesity, and diabetes.

12 Claims, 6 Drawing Sheets

FIG. 1

BLASTP - alignment of 49·g against swiss|P08635|SAST_RAT

This hit is scoring at : 3e-87 (expectation value)
    Alignment length (overlap) : 263
    Identities : 56 %
    Scoring matrix : BLOSUM62 (used to infer consensus pattern)
    Database searched : nrdb

```
Q:      1  MERGDQPKRTRNENIFNCLYKNPEATFKLICFPWMGGGSTHFAKWGQDTHDLLEVHSLRL
           ME.. ..K..RNE.:.NCLY:NP:A.FKLICFPW.GGGS.HFAKWGQ..:D LEVH::RL
H:      1  METAVNAKSPRNEKVLNCLYQNPDAVFKLICFPWAGGGSIHFAKWGQKINDSLEVHAVRL

PGRESRVEEPLENDISQLVDEVVCALQPVIQDKPFAFFGHSMGSYIAFRTALGLKENNQP
           .GRE:R: EP..NDI Q:.DE:V.AL P:IQDK.FAFFGHS.GSYIA. TAL LKE. :
           AGRETRLGEPFANDIYQIADEIVTALLPIIQDKAFAFFGHSFGSYIALITALLLKEKYKM

EPLHLFLSSATPVHSKAWHRIPKDDELSEEQISHYLMEFGGTPKHFAEAKEFVKQCSPII
           EPLH:F:S.A:. HS.:   ::P. :EL:EEQ:.H:L::FGGTPKH..E ::.::.  P::
           EPLHIFVSGASAPHSTSRPQVPDLNELTEEQVRHHLLDFGGTPKHLIEDQDVLRMFIPLL

RADLNIVRSCTSNVPSKAVLSCDLTCFVGSEDIAKDMEAWKDVTSGNAKIYQLPGGHFYL
           :AD..:V:. . : PSKA:LS.D:T F:GSED..KD:E.W:D:TSG. .:..LPG.HFYL
           KADAGVVKKFIFDKPSKALLSLDITGFLGSEDTIKDIEGWQDLTSGKFDVHMLPGDHFYL

LDPANEKLIKNYIIKCLEVSSIS        263
           :.P NE..IKNYI.KCLE:SS::
           MKPDNENFIKNYIAKCLELSSLT        263
```

FIG. 2

HMMPFAM - alignment of 49•g against pfam|hmm|Thioesterase

This hit is scoring at : 178.0   Expect = 1.6e-49
    Scoring matrix : BLOSUM62 (used to infer consensus pattern)

```
Q:     27 FKLICFPWMGG-GSTHFAKWGQDTHD-LLEVHSLRLPGRESRVEEPLENDISQLVDEVVC
          .L.CFP .GG .:::F.. .: . . L:EV.:::LPGRE.R   EPL ..I.:L.:E..
H:      1 rpLfcfPpAgGgsasyfrnlaralpgtlvevsavqlPgredRrgEplltsieelaeeyae ALQPVIQDK---PFAFFGHSMGSYIAFRTALGLKEN--NQPEPLHLFLSSATPVHSKAWH
          AL:..: .:   P:A.FGHSMG..:AF..A L:..  . .E   L.LS.A . :.. .
          alraiqpeGdivPYaLfGhSmGGllAfEvArrLerrqdgGeevsgLilsDayaPytterr RIPKDDELSEEQ------------ISHYLMEFGGT-PKHFAEAKEFVKQCSPIIRADLNI
          ....     .E.                : L...GGT P....E :E.:.  . P.:RAD...
          eashllgddetgnaleeaesvsqallaelrrlggtkppelledeellslaLpalradyra VRSCTsnVPSKAVLSCDLTCFVGSEDIAKDME------A-----------WKDVTSGNAK
          ::: .   .... S. .T.F.G::D ...::        .            W::.T.G .
          letyr..avpieapsvratlfygaddplatldgllaadrtkaygevgedrWreytpgafd IYQLPGGHFYLLDpAN--EKLIKNYIIKCL     257
          : .LPG.HFYLL: :    :  : .:I:..L
          vrmlpGdHFylle.dhveleevlehilral     267
```

FIG. 4

Alignment short vs. long (GCG GAP)

```
  1 MERGDQPKRTRNENIFNCLYKNPEATFKLICFPWMGGGSTHFAKWGQDTH  50
    |||||||||||||||||||||||||||||||||||||||||||||||||
  1 MERGDQPKRTRNENIFNCLYKNPEATFKLICFPWMGGGSTHFAKWGQDTH  50

51 DLLEETASHHVAKAGLKLRRSSDPPASAYPCAGVSHRRREPPCLAKILGL 100
    ||||
 51 DLLE.............................................  54

101 FWILIFFMHSLRLPGRESRVEEPLENDISQLVDEVVCALQPVIQDKPFAF 150
           .|||||||||||||||||||||||||||||||||||||||||
 55 .......VHSLRLPGRESRVEEPLENDISQLVDEVVCALQPVIQDKPFAF  97

151 FGHSMGSYIAFRTALGLKENNQPEPLHLFLSSATPVHSKAWHRIPKDDEL 200
    |||||||||||||||||||||||||||||||||||||||||||||||||
 98 FGHSMGSYIAFRTALGLKENNQPEPLHLFLSSATPVHSKAWHRIPKDDEL 147

201 SEEQISHYLMEFGGTPKHFAEAKEFVKQCSPIIRADLNIVRSCTSNVPSK 250
    |||||||||||||||||||||||||||||||||||||||||||||||||
148 SEEQISHYLMEFGGTPKHFAEAKEFVKQCSPIIRADLNIVRSCTSNVPSK 197

251 AVLSCDLTCFVGSEDIAKDMEAWKDVTSGNAKIYQLPGGHFYLLDPANEK 300
    |||||||||||||||||||||||||||||||||||||||||||||||||
198 AVLSCDLTCFVGSEDIAKDMEAWKDVTSGNAKIYQLPGGHFYLLDPANEK 247

301 LIKNYIIKCLEVSSISNF 318
    ||||||||||||||||||
248 LIKNYIIKCLEVSSISNF 266
```

REGULATION OF HUMAN S-ACYL FATTY ACID SYNTHASE THIOESTERASE-LIKE ENZYME

This application claims the benefit of and incorporates by reference co-pending provisional applications Serial No. 60/214,012 filed Jun. 26, 2000 and Serial No. 60/255,148 filed Dec. 14, 2000, and PCT/EP01/07297 filed Jun. 26, 2001.

TECHNICAL FIELD OF THE INVENTION

The invention relates to the area of regulation of human S-acyl fatty acid synthase thioesterase-like enzyme to provide therapeutic effects.

BACKGROUND OF THE INVENTION

The substrate specificity of fatty acid synthase can be modulated through the modification of fatty acid synthase by the enzyme S-acyl fatty acid synthase thioesterase. This modification causes fatty acid synthesis to be shifted from long chain fatty acids, which typically have 16, 18 or more carbon atoms in the fatty acid carbon chain, to medium chain fatty acids, typically having between 8–14 carbon atoms in the fatty acid chain. See U.S. Pat. No. 5,147,792. For example, rat medium-chain specific S-acyl fatty acid synthase thioesterase modulates the substrate specificity of fatty acid synthase through the preferential fatty acid chain termination, via premature release from the fatty acid synthase multifunctional complex (1) of a growing acyl chain. This reaction also has been observed in a transgenic plant (2).

In humans, the complex regulation of lipid metabolism involves various fatty acids and dietary triglycerides. Because medium chain fatty acids contribute to raising low density lipoprotein (LDL) blood cholesterol levels (3, 4, 5) in humans, they are generally undesirable. High levels of LDL blood cholesterol in turn have been implicated as associated with a number of conditions and diseases, including cardiovascular disease, hyperlipidemia, obesity, and diabetes. Regulation of S-fatty acid synthase thioesterase to lower LDL levels therefore has important implications for treatment of these.

SUMMARY OF THE INVENTION

It is an object of the invention to provide reagents and methods of regulating a human S-acyl fatty acid synthase thioesterase-like enzyme. This and other objects of the invention are provided by one or more of the embodiments described below.

One embodiment of the invention is a cDNA encoding a polypeptide comprising an amino acid sequence selected from the group consisting of SEQ ID NOS:2, 14, and 16.

Another embodiment of the invention is an expression vector comprising a polynucleotide which encodes a polypeptide comprising an amino acid sequence selected from the group consisting of SEQ ID NOS:2, 14, and 16.

Yet another embodiment of the invention is a host cell comprising an expression vector which encodes a polypeptide comprising an amino acid sequence selected from the group consisting of SEQ ID NOS:2, 14, and 16.

A further embodiment of the invention is a purified polypeptide comprising an amino acid sequence selected from the group consisting of SEQ ID NOS:2, 14, and 16.

Still another embodiment of the invention is a fusion protein comprising a polypeptide consisting of an amino acid sequence selected from the group consisting of SEQ ID NOS:2, 14, and 16.

Even another embodiment of the invention is a method of producing a polypeptide comprising an amino acid sequence selected from the group consisting of SEQ ID NOS:2, 14, and 16. A host cell comprising an expression vector which encodes the polypeptide is cultured under conditions whereby the polypeptide is expressed. The polypeptide is isolated.

Yet another embodiment of the invention is a method of detecting a coding sequence for a polypeptide comprising an amino acid sequence selected from the group consisting of SEQ ID NOS:2, 14, and 16. A polynucleotide comprising 11 contiguous nucleotides of SEQ ID NOS:12, 13, or 14 is hybridized to nucleic acid material of a biological sample, thereby forming a hybridization complex. The hybridization complex is detected.

Still another embodiment of the invention is a kit for detecting a coding sequence for a polypeptide comprising an amino acid sequence selected from the group consisting of SEQ ID NOS:2, 14, and 16. The kit comprises a polynucleotide comprising 11 contiguous nucleotides of SEQ ID NOS:12, 13, or 14 and instructions for detecting the coding sequence.

Even another embodiment of the invention is a method of detecting a polypeptide comprising an amino acid sequence selected from the group consisting of SEQ ID NOS:2, 14, and 16. A biological sample is contacted with a reagent that specifically binds to the polypeptide to form a reagent-polypeptide complex. The reagent-polypeptide complex is detected.

A further embodiment of the invention is a kit for detecting a polypeptide comprising an amino acid sequence selected from the group consisting of SEQ ID NOS:2, 14, and 16. The kit comprises an antibody which specifically binds to the polypeptide and instructions for detecting the polypeptide.

Another embodiment of the invention is a method of screening for agents that can regulate the activity of an S-acyl fatty acid synthase thioesterase-like enzyme. A test compound is contacted with a polypeptide comprising an amino acid sequence selected from the group consisting of: (1) amino acid sequences which are at least about 50% identical to an amino acid sequence selected from the group consisting of SEQ ID NOS:2, 14, and 16 and (2) the amino acid sequences shown in SEQ ID NOS:2, 14, and 16. Binding of the test compound to the polypeptide is detected. A test compound that binds to the polypeptide is thereby identified as a potential agent for regulating activity of the S-acyl fatty acid synthase thioesterase-like enzyme.

Even another embodiment of the invention is a method of screening for agents which regulate an activity of a human the S-acyl fatty acid synthase thioesterase-like enzyme. A test compound is contacted with a polypeptide comprising an amino acid sequence selected from the group consisting of: (1) amino acid sequences which are at least about 50% identical to an amino acid sequence selected from the group consisting of SEQ ID NOS:2, 14, and 16 and (2) the amino acid sequences shown in SEQ ID NOS:2, 14, and 16. An activity of the polypeptide is detected. A test compound that increases the activity of the polypeptide is thereby identified as a potential agent for increasing the activity of the human S-acyl fatty acid synthase thioesterase-like enzyme. A test compound that decreases the activity of the polypeptide is thereby identified as a potential agent for decreasing the activity of the human S-acyl fatty acid synthase thioesterase-like enzyme.

A further embodiment of the invention is a method of screening for agents that regulate an activity of a human S-acyl fatty acid synthase thioesterase-like enzyme. A test compound is contacted with a product encoded by a polynucleotide which comprises a nucleotide sequence selected from the group consisting of SEQ ID NOS:12, 13, and 15. Binding of the test compound to the product is detected. A test compound that binds to the product is thereby identified as a potential agent for regulating the activity of the human S-acyl fatty acid synthase thioesterase-like enzyme.

Still another embodiment of the invention is a method of reducing activity of a human S-acyl fatty acid synthase thioesterase-like enzyme. A cell is contacted with a reagent which specifically binds to a product encoded by a polynucleotide comprising the nucleotide sequence shown in SEQ ID NO: 1. The activity of a human S-acyl fatty acid synthase thioesterase-like enzyme is thereby reduced.

Another embodiment of the invention is a pharmaceutical composition, comprising a reagent which specifically binds to a polypeptide comprising an amino acid sequence selected from the group consisting of SEQ ID NOS:2, 14, and 16 and a pharmaceutically acceptable carrier.

Still another embodiment of the invention is a pharmaceutical composition. A reagent that specifically binds to a product of a polynucleotide comprising a nucleotide sequence selected from the group consisting of SEQ ID NOS:12, 13, and 15 and a pharmaceutically acceptable carrier.

Even another embodiment of the invention is a pharmaceutical composition comprising an expression vector encoding a polypeptide comprising an amino acid sequence selected from the group consisting of SEQ ID NOS:2, 14, and 16 and a pharmaceutically acceptable carrier.

Yet another embodiment of the invention is a method of treating a disorder selected from the group consisting of cardiovascular disease, hyperlipidemia, obesity, and diabetes. A therapeutically effective dose of a reagent that inhibits a function of a human S-acyl fatty acid synthase thioesterase-like enzyme is administered to a patient in need thereof. Symptoms of the disorder are thereby ameliorated.

A further embodiment of the invention is an isolated polynucleotide selected from the group consisting of: (a) a polynucleotide encoding a protein that comprises an amino acid sequence selected from the group consisting of SEQ ID NOS:2, 14, and 16, (b) a polynucleotide comprising a nucleotide selected from the group consisting of SEQ ID NOs:12, 13, and 15, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Yet another embodiment of the invention is an expression vector comprising a polynucleotide selected from the group consisting of: (a) a polynucleotide encoding a protein that comprises an amino acid sequence selected from the group consisting of SEQ ID NOS:2, 14, and 16, (b) a polynucleotide comprising a nucleotide selected from the group consisting of SEQ ID NOs:12, 13, and 15, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Even another embodiment of the invention is a host cell comprising an expression vector comprising a polynucleotide selected from the group consisting of: (a) a polynucleotide encoding a protein that comprises an amino acid sequence selected from the group consisting of SEQ ID NOS:2, 14, and 16, (b) a polynucleotide comprising a nucleotide selected from the group consisting of SEQ ID NOs:12, 13, and 15, (c) a polynucleotide which hybridizes under stringent conditions to a polynucleotide specified in (a) or (b); (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

Still another embodiment of the invention is a preparation of antibodies that specifically bind to a polypeptide selected from the group consisting of (a) an amino acid sequence selected from the group consisting of SEQ ID NOS:2, 14, and 16 and (b) biologically active variants thereof.

Yet another embodiment of the invention is an antisense oligonucleotide that hybridizes to a polynucleotide selected from the group consisting of (a) a polynucleotide encoding a protein that comprises an amino acid sequence selected from the group consisting of SEQ ID NOS:2, 14, and 16, (b) a polynucleotide comprising a nucleotide sequence selected from the group consisting of SEQ ID NOS:12, 13, and 15, (c) a polynucleotide which hybridizes under stringent conditions to a polynucleotide specified in (a) or (b), (d) a polynucleotide having a nucleic acid sequence that deviates from the nucleic acid sequences specified in (a)–(c) due to the degeneration of the genetic code, and (e) a polynucleotide that represents a fragment, derivative, or allelic variation of a nucleic acid sequence specified in (a)–(d).

The invention thus provides a human S-acyl fatty acid synthase thioesterase-like enzyme which can be used to identify test compounds which may act, for example, as agonists or antagonists at the enzyme's active site. Human S-acyl fatty acid synthase thioesterase-like enzyme and fragments thereof also are useful in raising specific antibodies which can block the enzyme and effectively reduce its activity.

BRIEF DESCRIPTION OF THE DRAWINGS

FIG. 1. BLASTP alignment of human S-acyl fatty acid synthase thioesterase-like enzyme (SEQ ID NO:2) with the rat protein identified by SwissProt Accession No. P08635 (SEQ ID NO:3) as S-acyl fatty acid synthase thioesterase.

FIG. 2. HMMPFAM alignment of human S-acyl fatty acid synthase thioesterase-like enzyme (SEQ ID NO:2) with the Pfam Accession No. PF00975 (SEQ ID NO:4) hmm thioesterase.

FIG. 4. Alignment of S-acyl fatty acid synthase thioesterase-like enzyme "short" (SEQ ID NO:14) and "long" (SEQ ID NO:16) polypeptides.

DETAILED DESCRIPTION OF THE INVENTION

Figure 3:
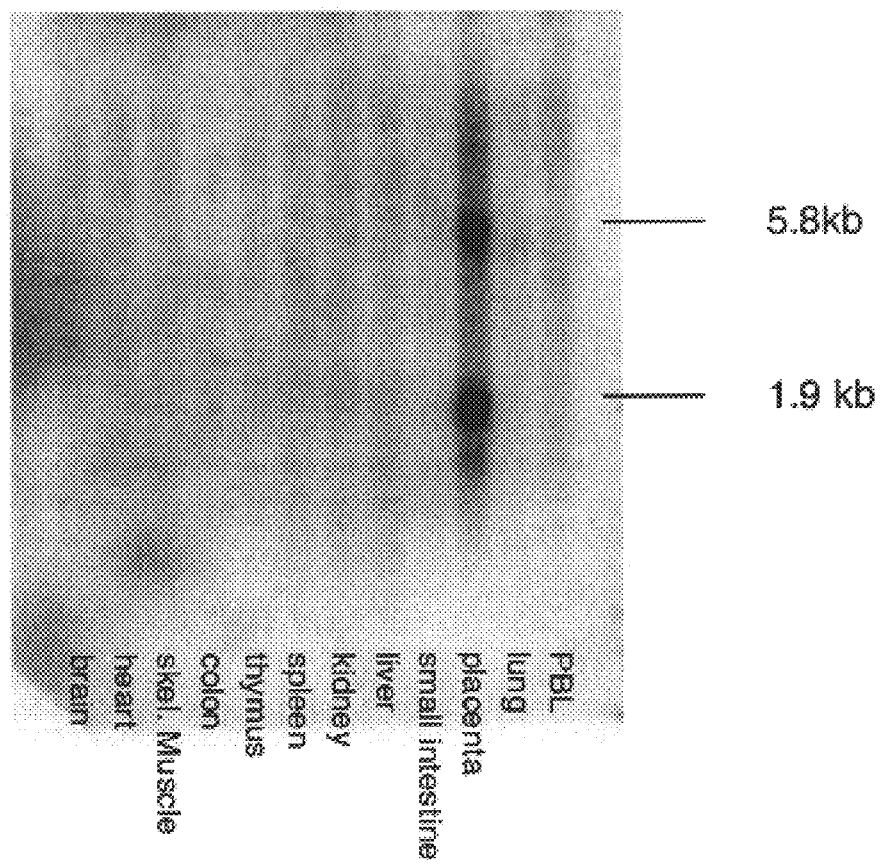
FIG. 3. Northern blot of tissue-specific expression of S-acyl fatty acid synthase thioesterase-like enzyme.

A novel human S-acyl fatty acid synthase thioesterase-like enzyme is a discovery of the present invention. Human S-acyl fatty acid synthase thioesterase-like enzyme comprises the amino acid sequence shown in SEQ ID NO:2, as encoded by the coding sequence shown in SEQ ID NO:12; this coding sequence is contained within the genomic clone identified with GenBank Accession No. AK001844, as shown in SEQ ID NO:1. A number of ESTs are contained within the coding sequence of human S-acyl fatty acid synthase thioesterase-like enzyme, indicating that SEQ ID NO:12 is expressed (SEQ ID NOS:7–11).

Human S-acyl fatty acid synthase thioesterase-like enzyme is 56% identical over a 263 amino acid overlap to the rat protein identified by SwissProt Accession No. P08635 (SEQ ID NO:3) and annotated as S-acyl fatty acid synthase thioesterase (FIG. 1). Human S-acyl fatty acid synthase thioesterase-like enzyme also contains many identities to amino acids present in a hidden Markov model (hmm) of thioesterase domains derived from 76 thioesterases, as shown in FIG. 2.

The human S-acyl fatty acid synthase thioesterase-like enzyme of the invention is expected to be useful for the same purposes as previously identified S-acyl fatty acid synthase thioesterase enzymes. Thus, human S-acyl fatty acid synthase thioesterase-like enzyme can be used in therapeutic methods to treat disorders such as cardiovascular disease, hyperlipidemia, obesity, and diabetes. Human S-acyl fatty acid synthase thioesterase-like enzyme also can be used to screen for human S-acyl fatty acid synthase thioesterase-like enzyme agonists and antagonists.

Polypeptides

S-acyl fatty acid synthase thioesterase-like enzyme polypeptides according to the invention comprise at least 12, 15, 25, 50, 75, 100, 125, 150, 175, 200, 225, 250 or 265 contiguous amino acids selected from the amino acid sequence shown in SEQ ID NO:2 or a biologically active variant thereof, as defined below. An S-acyl fatty acid synthase thioesterase-like enzyme polypeptide of the invention therefore can be a portion of an S-acyl fatty acid synthase thioesterase-like enzyme protein, a full-length S-acyl fatty acid synthase thioesterase-like enzyme protein, or a fusion protein comprising all or a portion of an S-acyl fatty acid synthase thioesterase-like enzyme protein.

Biologically Active Variants

S-acyl fatty acid synthase thioesterase-like enzyme polypeptide variants which are biologically active, i.e., retain an S-acyl fatty acid synthase thioesterase-like activity, also are S-acyl fatty acid synthase thioesterase-like enzyme polypeptides. Preferably, naturally or non-naturally occurring S-acyl fatty acid synthase thioesterase-like enzyme polypeptide variants have amino acid sequences which are at least about 55, 60, 65, or 70, preferably about 75, 80, 85, 90, 96, 96, or 98% identical to the amino acid sequence shown in SEQ ID NO:2 or a fragment thereof. Percent identity between a putative S-acyl fatty acid synthase thioesterase-like enzyme polypeptide variant and an amino acid sequence of SEQ ID NO:2 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an S-acyl fatty acid synthase thioesterase-like enzyme polypeptide can be found using computer programs well known in the art, such as DNASTAR software. Whether an amino acid change results in a biologically active S-acyl fatty acid synthase thioesterase-like enzyme polypeptide can readily be determined by assaying for S-acyl fatty acid synthase thioesterase activity, as described for example, in the specific Examples, below.

Fusion Proteins

Fusion proteins are useful for generating antibodies against S-acyl fatty acid synthase thioesterase-like enzyme polypeptide amino acid sequences and for use in various assay systems. For example, fusion proteins can be used to identify proteins which interact with portions of an S-acyl fatty acid synthase thioesterase-like enzyme polypeptide. Protein affinity chromatography or library-based assays for protein—protein interactions, such as the yeast two-hybrid or phage display systems, can be used for this purpose. Such methods are well known in the art and also can be used as drug screens.

An S-acyl fatty acid synthase thioesterase-like enzyme polypeptide fusion protein comprises two polypeptide segments fused together by means of a peptide bond. For example, the first polypeptide segment can comprise at least 12, 15, 25, 50, 75, 100, 125, 150, 175, 200, 225, or 250 contiguous amino acids of SEQ ID NO:2 or of a biologically active variant, such as those described above. The first polypeptide segment also can comprise full-length S-acyl fatty acid synthase thioesterase-like enzyme protein.

The second polypeptide segment can be a full-length protein or a protein fragment. Proteins commonly used in fusion protein construction include .-galactosidase, .-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the S-acyl fatty acid synthase thioesterase-like enzyme polypeptide-encoding sequence and the heterologous protein sequence, so that the S-acyl fatty acid synthase thioesterase-like enzyme polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO:12 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human S-acyl fatty acid synthase thioesterase-like enzyme polypeptide can be obtained using S-acyl fatty acid synthase thioesterase-like enzyme polypeptide polynucleotides (described below) to make suitable probes or primers for screening cDNA expression libraries from other species, such as mice, monkeys, or yeast, identifying cDNAs which encode homologs of S-acyl fatty acid synthase thioesterase-like enzyme polypeptide, and expressing the cDNAs as is known in the art.

Polynucleotides

An S-acyl fatty acid synthase thioesterase-like enzyme polynucleotide can be single- or double-stranded and comprises a coding sequence or the complement of a coding sequence for an S-acyl fatty acid synthase thioesterase-like enzyme polypeptide. A coding sequence for human S-acyl fatty acid synthase thioesterase-like enzyme of SEQ ID NO:2 is shown in SEQ ID NO:12.

Degenerate nucleotide sequences encoding human S-acyl fatty acid synthase thioesterase-like enzyme polypeptides, as well as homologous nucleotide sequences which are at least about 50, 55, 60, 65, 60, preferably about 75, 90, 96, or 98% identical to the nucleotide sequence shown in SEQ ID NO:12 also are S-acyl fatty acid synthase thioesterase-like enzyme polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of S-acyl fatty acid synthase thioesterase-like enzyme polynucleotides which encode biologically active S-acyl fatty acid synthase thioesterase-like enzyme polypeptides also are S-acyl fatty acid synthase thioesterase-like enzyme polynucleotides.

Identification of Polynucleotide Variants and Homologs

Variants and homologs of the S-acyl fatty acid synthase thioesterase-like enzyme polynucleotides described above also are S-acyl fatty acid synthase thioesterase-like enzyme polynucleotides. Typically, homologous S-acyl fatty acid synthase thioesterase-like enzyme polynucleotide sequences can be identified by hybridization of candidate polynucleotides to known S-acyl fatty acid synthase thioesterase-like enzyme polynucleotides under stringent conditions, as is known in the art. For example, using the following wash conditions: 2× SSC (0.3 M NaCl, 0.03 M sodium citrate, pH 7.0), 0.1% SDS, room temperature twice, 30 minutes each; then 2× SSC, 0.1% SDS, 50° C. once, 30 minutes; then 2× SSC, room temperature twice, 10 minutes each homologous sequences can be identified which contain at most about 2530% basepair mismatches. More preferably, homologous nucleic acid strands contain 1525% basepair mismatches, even more preferably 515% basepair mismatches.

Species homologs of the S-acyl fatty acid synthase thioesterase-like enzyme polynucleotides disclosed herein also can be identified by making suitable probes or primers and screening cDNA expression libraries from other species, such as mice, monkeys, or yeast. Human variants of S-acyl fatty acid synthase thioesterase-like enzyme polynucleotides can be identified, for example, by screening human cDNA expression libraries. It is well known that the Tm of a double-stranded DNA decreases by 1–1.5° C. with every 1% decrease in homology (Bonner et al., *J. Mol. Biol.* 81, 123 (1973). Variants of human S-acyl fatty acid synthase thioesterase-like enzyme polynucleotides or S-acyl fatty acid synthase thioesterase-like enzyme polynucleotides of other species can therefore be identified by hybridizing a putative homologous S-acyl fatty acid synthase thioesterase-like enzyme polynucleotide with a polynucleotide having a nucleotide sequence of SEQ ID NO: 12 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to S-acyl fatty acid synthase thioesterase-like enzyme polynucleotides or their complements following stringent hybridization and/or wash conditions also are S-acyl fatty acid synthase thioesterase-like enzyme polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between an S-acyl fatty acid synthase thioesterase-like enzyme polynucleotide having a nucleotide sequence shown in SEQ ID NO:12 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% G+C) - 0.63(\% \text{formamide}) - 600/l),$$

where l=the length of the hybrid in basepairs.

Stringent wash conditions include, for example, 4× SSC at 65° C., or 50% formamide, 4× SSC at 42° C., or 0.5× SSC, 0.1% SDS at 65° C. Highly stringent wash conditions include, for example, 0.2× SSC at 65° C.

Preparation of Polynucleotides

A naturally occurring S-acyl fatty acid synthase thioesterase-like enzyme polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated S-acyl fatty acid synthase thioesterase-like enzyme polynucleotides. For example, restriction enzymes and probes can be used to isolate polynucleotide fragments which comprises S-acyl fatty acid synthase thioesterase-like enzyme nucleotide sequences. Isolated polynucleotides are in preparations which are free or at least 70, 80, or 90% free of other molecules.

S-acyl fatty acid synthase thioesterase-like enzyme cDNA molecules can be made with standard molecular biology techniques, using S-acyl fatty acid synthase thioesterase-like enzyme mRNA as a template. S-acyl fatty acid synthase thioesterase-like enzyme cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesizes S-acyl fatty acid synthase thioesterase-like enzyme polynucleotides. The degeneracy of the genetic code allows alternate nucleotide sequences to be synthesized which will encode an S-acyl fatty acid synthase thioesterase-like enzyme polypeptide having, for example, an amino acid sequence shown in SEQ ID NO:2 or a biologically active variant thereof.

Extending Polynucleotides

Various PCR-based methods can be used to extend the nucleic acid sequences disclosed herein to detect upstream sequences such as promoters and regulatory elements. For example, restriction site PCR uses universal primers to retrieve unknown sequence adjacent to a known locus (Sarkar, PCR Methods Applic. 2, 318322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 2230 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., PCR Methods Applic. 1, 11119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 30553060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' nontranscribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

S-acyl fatty acid synthase thioesterase-like enzyme polypeptides can be obtained, for example, by purification from human cells, by expression of S-acyl fatty acid synthase thioesterase-like enzyme polynucleotides, or by direct chemical synthesis.

Protein Purification

S-acyl fatty acid synthase thioesterase-like enzyme polypeptides can be purified from any cell which expresses the enzyme, including host cells which have been transfected with S-acyl fatty acid synthase thioesterase-like enzyme expression constructs. Fetal kidney, brain and liver provides an especially useful source of S-acyl fatty acid synthase thioesterase-like enzyme polypeptides. A purified S-acyl fatty acid synthase thioesterase-like enzyme polypeptide is separated from other compounds which normally associate with the S-acyl fatty acid synthase thioesterase-like enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified S-acyl fatty acid synthase thioesterase-like enzyme polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express an S-acyl fatty acid synthase thioesterase-like enzyme polynucleotide, the polynucleotide can be inserted into an expression vector which contains the necessary elements for the transcription and translation of the inserted coding sequence. Methods which are well known to those skilled in the art can be used to construct expression vectors containing sequences encoding S-acyl fatty acid synthase thioesterase-like enzyme polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding an S-acyl fatty acid synthase thioesterase-like enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an S-acyl fatty acid synthase thioesterase-like enzyme polypeptide, vectors based on SV40 or EBV can be used with an appropriate selectable marker.

Bacterial and Yeast Expression Systems

In bacterial systems, a number of expression vectors can be selected depending upon the use intended for the S-acyl fatty acid synthase thioesterase-like enzyme polypeptide. For example, when a large quantity of an S-acyl fatty acid synthase thioesterase-like enzyme polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the S-acyl fatty acid synthase thioesterase-like enzyme polypeptide can be ligated into the vector in frame with sequences for the amino terminal Met and the subsequent 7 residues of .-galactosidase so that a hybrid protein is produced. pIN vectors (Van Heeke & Schuster, *J. Biol. Chem.* 264, 55035509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516544, 1987.

Plant and Insect Expression Systems

If plant expression vectors are used, the expression of sequences encoding S-acyl fatty acid synthase thioesterase-like enzyme polypeptides can be driven by any of a number of promoters. For example, viral promoters such as the 35S and 19S promoters of CaMV can be used alone or in combination with the omega leader sequence from TMV (Takamatsu, *EMBO J.* 6, 307311, 1987). Alternatively, plant promoters such as the small subunit of RUBISCO or heat shock promoters can be used (Coruzzi et al., *EMBO J* 3, 16711680, 1984; Broglie et al., *Science* 224, 838843, 1984; Winter et al., *Results Probl. Cell Differ.* 17, 85105, 1991). These constructs can be introduced into plant cells by direct DNA transformation or by pathogen-mediated transfection. Such techniques are described in a number of generally available reviews (e.g., Hobbs or Murray, in McGraw HILL YEARBOOK OF SCIENCE AND TECHNOLOGY, McGraw Hill, New York, N.Y., pp. 191196, 1992).

An insect system also can be used to express an S-acyl fatty acid synthase thioesterase-like enzyme polypeptide. For example, in one such system *Autographa califormica* nuclear polyhedrosis virus (AcNPV) is used as a vector to express foreign genes in *Spodoptera frugiperda* cells or in Trichoplusia larvae. Sequences encoding S-acyl fatty acid synthase thioesterase-like enzyme polypeptides can be cloned into a nonessential region of the virus, such as the polyhedrin gene, and placed under control of the polyhedrin promoter. Successful insertion of S-acyl fatty acid synthase thioesterase-like enzyme polypeptides will render the polyhedrin gene inactive and produce recombinant virus lacking coat protein. The recombinant viruses can then be used to infect *S. frugiperda* cells or Trichoplusia larvae in which S-acyl fatty acid synthase thioesterase-like enzyme polypeptides can be expressed (Engelhard et al., *Proc. Nat. Acad. Sci.* 91, 32243227, 1994).

Mammalian Expression Systems

A number of viral-based expression systems can be used to express S-acyl fatty acid synthase thioesterase-like enzyme polypeptides in mammalian host cells. For example, if an adenovirus is used as an expression vector, sequences encoding S-acyl fatty acid synthase thioesterase-like enzyme polypeptides can be ligated into an adenovirus transcription/translation complex comprising the late promoter and tripartite leader sequence. Insertion in a nonessential E1 or E3 region of the viral genome can be used to obtain a viable virus that is capable of expressing an S-acyl fatty acid synthase thioesterase-like enzyme polypeptide in infected host cells (Logan & Shenk, *Proc. Natl. Acad. Sci.* 81, 36553659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding S-acyl fatty acid synthase thioesterase-like enzyme polypeptides. Such signals include the ATG initiation codon and adjacent sequences. In cases where sequences encoding an S-acyl fatty acid synthase thioesterase-like enzyme polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125162, 1994).

Host Cells

A host cell strain can be chosen for its ability to modulate the expression of the inserted sequences or to process the expressed S-acyl fatty acid synthase thioesterase-like enzyme polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high yield production of recombinant proteins. For example, cell lines which stably express S-acyl fatty acid synthase thioesterase-like enzyme polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced S-acyl fatty acid synthase thioesterase-like enzyme sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines. These include, but are not limited to, the herpes simplex virus thymidine kinase (Wigler et al., Cell 11, 22332, 1977) and adenine phosphoribosyltransferase (Lowy et al., Cell 22, 81723, 1980) genes which can be employed in tk⁻ or aprf cells, respectively. Also, antimetabolite, antibiotic, or herbicide resistance can be used as the basis for selection. For example, dhfr confers resistance to methotrexate (Wigler et al., Proc. Natl. Acad. Sci. 77, 356770, 1980), npt confers resistance to the aminoglycosides, neomycin and G418 (Colbere-Garapin et al., J. Mol. Biol. 150, 114, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, Proc. Natl. Acad. Sci. 85, 804751, 1988). Visible markers such as anthocyanins, __-glucuronidase and its substrate GUS, and luciferase and its substrate luciferin, can be used to identify transformants and to quantify the amount of transient or stable protein expression attributable to a specific vector system (Rhodes et al., Methods Mol. Biol. 55, 121131, 1995).

Detecting Expression

Although the presence of marker gene expression suggests that the S-acyl fatty acid synthase thioesterase-like enzyme polynucleotide is also present, its presence and expression may need to be confirmed. For example, if a sequence encoding an S-acyl fatty acid synthase thioesterase-like enzyme polypeptide is inserted within a marker gene sequence, transformed cells containing sequences which encode an S-acyl fatty acid synthase thioesterase-like enzyme polypeptide can be identified by the absence of marker gene function. Alternatively, a marker gene can be placed in tandem with a sequence encoding an S-acyl fatty acid synthase thioesterase-like enzyme polypeptide under the control of a single promoter. Expression of the marker gene in response to induction or selection usually indicates expression of the S-acyl fatty acid synthase thioesterase-like enzyme polynucleotide.

Alternatively, host cells which contain an S-acyl fatty acid synthase thioesterase-like enzyme polynucleotide and which express an S-acyl fatty acid synthase thioesterase-like enzyme polypeptide can be identified by a variety of procedures known to those of skill in the art. These procedures include, but are not limited to, DNA—DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding an S-acyl fatty acid synthase thioesterase-like enzyme polypeptide can be detected by DNA—DNA or DNA-RNA hybridization or amplification using probes or fragments or fragments of polynucleotides encoding an S-acyl fatty acid synthase thioesterase-like enzyme polypeptide. Nucleic acid amplification-based assays involve the use of oligonucleotides selected from sequences encoding an S-acyl fatty acid synthase thioesterase-like enzyme polypeptide to detect transformants which contain an S-acyl fatty acid synthase thioesterase-like enzyme polynucleotide.

A variety of protocols for detecting and measuring the expression of an S-acyl fatty acid synthase thioesterase-like enzyme polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on an S-acyl fatty acid synthase thioesterase-like enzyme polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 12111216, 1983).

A wide variety of labels and conjugation techniques are known by those skilled in the art and can be used in various nucleic acid and amino acid assays. Means for producing labeled hybridization or PCR probes for detecting sequences related to polynucleotides encoding S-acyl fatty acid synthase thioesterase-like enzyme polypeptides include oligolabeling, nick translation, end-labeling, or PCR amplification using a labeled nucleotide. Alternatively, sequences encoding an S-acyl fatty acid synthase thioesterase-like enzyme polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding an S-acyl fatty acid synthase thioesterase-like enzyme polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode S-acyl fatty acid synthase thioesterase-like enzyme polypeptides can be designed to contain signal sequences which direct secretion of soluble S-acyl fatty acid synthase thioesterase-like enzyme polypeptides through a prokaryotic or eukaryotic cell membrane or which direct the membrane insertion of membrane-bound S-acyl fatty acid synthase thioesterase-like enzyme polypeptide.

As discussed above, other constructions can be used to join a sequence encoding an S-acyl fatty acid synthase thioesterase-like enzyme polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the S-acyl fatty acid synthase thioesterase-like enzyme polypeptide also can be used to facilitate purification. One such expression vector provides for expression of a fusion protein containing an S-acyl fatty acid synthase thioesterase-like enzyme polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif* 3, 263281, 1992), while the enterokinase cleavage site provides a means for purifying the S-acyl fatty acid synthase thioesterase-like enzyme polypeptide from the fusion protein. Vectors which contain fusion proteins are disclosed in Kroll et al., *DNA Cell Biol.* 12, 441453, 1993.

Chemical Synthesis

Sequences encoding an S-acyl fatty acid synthase thioesterase-like enzyme polypeptide can be synthesized, in whole or in part, using chemical methods well known in the art (see Caruthers et al., *Nucl. Acids Res. Symp. Ser.* 215223, 1980; Horn et al. *Nucl. Acids Res. Symp. Ser.* 225232, 1980). Alternatively, an S-acyl fatty acid synthase thioesterase-like enzyme polypeptide itself can be produced using chemical methods to synthesize its amino acid sequence, such as by direct peptide synthesis using solid-phase techniques (Merrifield, *J. Am. Chem. Soc.* 85, 21492154, 1963; Roberge et al., *Science* 269, 202204, 1995). Protein synthesis can be performed using manual techniques or by automation. Automated synthesis can be achieved, for example, using Applied Biosystems 431A Peptide Synthesizer (Perkin Elmer). Optionally, fragments of S-acyl fatty acid synthase thioesterase-like enzyme polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic S-acyl fatty acid synthase thioesterase-like enzyme polypeptide can be confirmed by amino acid analysis or sequencing (e.g., the Edman degradation procedure; see Creighton, supra). Additionally, any portion of the amino acid sequence of the S-acyl fatty acid synthase thioesterase-like enzyme polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce S-acyl fatty acid synthase thioesterase-like enzyme polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter S-acyl fatty acid synthase thioesterase-like enzyme polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of an S-acyl fatty acid synthase thioesterase-like enzyme polypeptide. "Antibody" as used herein includes intact immunoglobulin molecules, as well as fragments thereof, such as Fab, $F(ab')_2$, and Fv, which are capable of binding an epitope of an S-acyl fatty acid synthase thioesterase-like enzyme polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an S-acyl fatty acid synthase thioesterase-like enzyme polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to an S-acyl fatty acid synthase thioesterase-like enzyme polypeptide provides a detection signal at least 5-, 10-, or 20-fold higher than a detection signal provided with other proteins when used in an immunochemical assay. Preferably, antibodies which specifically bind to S-acyl fatty acid synthase thioesterase-like enzyme polypeptides do not detect other proteins in immunochemical assays and can immunoprecipitate an S-acyl fatty acid synthase thioesterase-like enzyme polypeptide from solution.

S-acyl fatty acid synthase thioesterase-like enzyme polypeptides can be used to immunize a mammal, such as a mouse, rat, rabbit, guinea pig, monkey, or human, to produce polyclonal antibodies. If desired, an S-acyl fatty acid synthase thioesterase-like enzyme polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to an S-acyl fatty acid synthase thioesterase-like enzyme polypeptide can be prepared using any technique which provides for the production of antibody molecules by continuous cell lines in culture. These techniques include, but are not limited to, the hybridoma technique, the human B cell hybridoma technique, and the EBV hybridoma technique (Kohler et al., *Nature* 256, 495497, 1985; Kozbor et al., *J. Immunol. Methods* 81, 3142, 1985; Cote et al., *Proc. Natl. Acad. Sci.* 80, 20262030, 1983; Cole et al., *Mol. Cell Biol.* 62, 109120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 68516855, 1984; Neuberger et al., *Nature* 312, 604608, 1984; Takeda et al., *Nature* 314, 452454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies which specifically bind to an S-acyl fatty acid synthase thioesterase-like enzyme polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to S-acyl fatty acid synthase thioesterase-like enzyme polypeptides. Antibodies with related specificity, but of distinct idiotypic composition, can be generated by chain shuffling from random combinatorial immunoglobin libraries (Burton, *Proc. Natl. Acad. Sci.* 88, 1112023, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to S-acyl fatty acid synthase thioesterase-like enzyme polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 38333837, 1989; Winter et al., *Nature* 349, 293299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which an S-acyl fatty acid synthase thioesterase-like enzyme polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of S-acyl fatty acid synthase thioesterase-like enzyme gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol* 20, 18, 1994; Sonveaux, *Meth. Mol. Biol.* 26, 1–72, 1994; Uhlmann et al., *Chem. Rev.* 90, 543583, 1990.

Modifications of S-acyl fatty acid synthase thioesterase-like enzyme gene expression can be obtained by designing antisense oligonucleotides which will form duplexes to the control, 5', or regulatory regions of the S-acyl fatty acid synthase thioesterase-like enzyme gene. Oligonucleotides derived from the transcription initiation site, e.g., between positions 10 and +10 from the start site, are preferred. Similarly, inhibition can be achieved using "triple helix" base pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of an S-acyl fatty acid synthase thioesterase-like enzyme polynucleotide. Antisense oligonucleotides which comprise, for example, 2, 3, 4, or 5 or more stretches of contiguous nucleotides which are precisely complementary to an S-acyl fatty acid synthase thioesterase-like enzyme polynucleotide, each separated by a stretch of contiguous nucleotides which are not complementary to adjacent S-acyl fatty acid synthase thioesterase-like enzyme nucleotides, can provide sufficient targeting specificity for S-acyl fatty acid synthase thioesterase-like enzyme mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular S-acyl fatty acid synthase thioesterase-like enzyme polynucleotide sequence.

Antisense oligonucleotides can be modified without affecting their ability to hybridize to an S-acyl fatty acid synthase thioesterase-like enzyme polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5' substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152158, 1992; Uhlmann et al., *Chem. Rev.* 90, 543584, 1990; Uhlmann et al., Tetrahedron. Lett. 215, 35393542, 1987.

Ribozymes

Ribozymes are RNA molecules with catalytic activity. See, e.g., Cech, *Science* 236, 15321539; 1987; Cech, *Ann. Rev. Biochem.* 59, 543568; 1990, Cech, *Curr. Opin. Struct. Biol.* 2, 605609; 1992, Couture & Stinchcomb, *Trends Genet.* 12, 510515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of an S-acyl fatty acid synthase thioesterase-like enzyme polynucleotide can be used to generate ribozymes which will specifically bind to mRNA transcribed from the S-acyl fatty acid synthase thioesterase-like enzyme polynucleotide. Methods of designing and constructing ribozymes which can cleave other RNA molecules in trans in a highly sequence specific manner have been developed and described in the art (see Haseloff et al. *Nature* 334, 585591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within an S-acyl fatty acid synthase thioesterase-like enzyme RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate S-acyl fatty acid synthase thioesterase-like enzyme RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease S-acyl fatty acid synthase thioesterase-like enzyme expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human S-acyl fatty acid synthase thioesterase-like enzyme. Such genes may represent genes that are differentially expressed in disorders including, but not limited to, hyperlipidemia, cardiovascular disorders, diabetes, and obesity. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human S-acyl fatty acid synthase thioesterase-like enzyme gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., Proc. Natl. Acad. Sci. U.S.A. 85, 208–12, 1988), subtractive hybridization (Hedrick et al., Nature 308, 149–53; Lee et al., Proc. Natl. Acad. Sci. U.S.A. 88, 2825, 1984), and differential display (Liang & Pardee, Science 257, 967–71, 1992; U.S. Pat. No. 5,262,311), and microarrays.

The differential expression information may itself suggest relevant methods for the treatment of disorders involving the human S-acyl fatty acid synthase thioesterase-like enzyme. For example, treatment may include a modulation of expression of the differentially expressed genes and/or the gene encoding the human S-acyl fatty acid synthase thioesterase-like enzyme. The differential expression information may indicate whether the expression or activity of the differentially expressed gene or gene product or the human S-acyl fatty acid synthase thioesterase-like enzyme gene or gene product are up-regulated or down-regulated.

Screening Methods

The invention provides assays for screening test compounds which bind to or modulate the activity of an S-acyl fatty acid synthase thioesterase-like enzyme polypeptide or an S-acyl fatty acid synthase thioesterase-like enzyme polynucleotide. A test compound preferably binds to an S-acyl fatty acid synthase thioesterase-like enzyme polypeptide or polynucleotide. More preferably, a test compound decreases or increases S-acyl fatty acid synthase thioesterase activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. NatL. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412421, 1992), or on beads (Lam, Nature 354, 8284, 1991), chips (Fodor, Nature 364, 555556, 1993), bacteria or spores (Ladner, U.S. Pat. No. 5,223,409), plasmids (Cull et al., Proc. Natl. Acad. Sci. U.S.A. 89, 18651869, 1992), or phage (Scott & Smith, Science 249, 386390, 1990; Devlin, Science 249, 404406, 1990); Cwirla et al., Proc. Natl. Acad. Sci. 97, 63786382, 1990; Felici, J. Mol. Biol. 222, 301310, 1991; and Ladner, U.S. Pat. No. 5,223,409).

High Throughput Screening

Test compounds can be screened for the ability to bind to S-acyl fatty acid synthase thioesterase-like enzyme polypeptides or polynucleotides or to affect S-acyl fatty acid synthase thioesterase-like enzyme activity or S-acyl fatty acid synthase thioesterase-like enzyme gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 $\mu$l. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., Proc. Natl. Acad. Sci. U.S.A. 19, 161418 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (November 710, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV light. Compounds that inhibited the enzyme were observed as local zones of inhibition having less color change.

Yet another example is described by Salmon et al., Molecular Diversity 2, 5763 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies, for example, the active site of the S-acyl fatty acid synthase thioesterase-like enzyme polypeptide, such that normal biological activity is prevented. Examples of such small molecules include, but are not limited to, small peptides or peptide-like molecules.

In binding assays, either the test compound or the S-acyl fatty acid synthase thioesterase-like enzyme polypeptide can comprise a detectable label, such as a fluorescent, radioisotopic, chemiluminescent, or enzymatic label, such as horseradish peroxidase, alkaline phosphatase, or luciferase. Detection of a test compound which is bound to the S-acyl fatty acid synthase thioesterase-like enzyme polypeptide can then be accomplished, for example, by direct counting of radioemmission, by scintillation counting, or by determining conversion of an appropriate substrate to a detectable product.

Alternatively, binding of a test compound to an S-acyl fatty acid synthase thioesterase-like enzyme polypeptide can be determined without labeling either of the interactants. For example, a microphysiometer can be used to detect binding of a test compound with an S-acyl fatty acid synthase thioesterase-like enzyme polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and an S-acyl fatty acid synthase thioesterase-like enzyme polypeptide (McConnell et al., *Science* 257, 19061912, 1992).

Determining the ability of a test compound to bind to an S-acyl fatty acid synthase thioesterase-like enzyme polypeptide also can be accomplished using a technology such as real-time Bimolecular Interaction Analysis (BIA) (Sjolander & Urbaniczky, *Anal Chem.* 63, 23382345, 1991, and Szabo et al., *Curr. Opin. Struct. Biol.* 5, 699705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, an S-acyl fatty acid synthase thioesterase-like enzyme polypeptide can be used as a "bait protein" in a two-hybrid assay or three-hybrid assay (see, e.g., U.S. Pat. No. 5,283,317; Zervos et al., *Cell* 72, 223232, 1993; Madura et al., *J. Biol. Chem.* 268, 1204612054, 1993; Bartel et al., *BioTechniques* 14, 920924, 1993; Iwabuchi et al., *Oncogene* 8, 16931696, 1993; and Brent WO94/10300), to identify other proteins which bind to or interact with the S-acyl fatty acid synthase thioesterase-like enzyme polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding an S-acyl fatty acid synthase thioesterase-like enzyme polypeptide can be fused to a polynucleotide encoding the DNA binding domain of a known transcription factor (e.g., GAL4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-BINDING and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the S-acyl fatty acid synthase thioesterase-like enzyme polypeptide.

It may be desirable to immobilize either the S-acyl fatty acid synthase thioesterase-like enzyme polypeptide (or polynucleotide) or the test compound to facilitate separation of bound from unbound forms of one or both of the interactants, as well as to accommodate automation of the assay. Thus, either the S-acyl fatty acid synthase thioesterase-like enzyme polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the S-acyl fatty acid synthase thioesterase-like enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to an S-acyl fatty acid synthase thioesterase-like enzyme polypeptide (or polynucleotide) can be accomplished in any vessel suitable for containing the reactants. Examples of such vessels include microtiter plates, test tubes, and microcentrifuge tubes.

In one embodiment, the S-acyl fatty acid synthase thioesterase-like enzyme polypeptide is a fusion protein comprising a domain that allows the S-acyl fatty acid synthase thioesterase-like enzyme polypeptide to be bound to a solid support. For example, glutathione S-transferase fusion proteins can be adsorbed onto glutathione sepharose beads (Sigma Chemical, St. Louis, Mo.) or glutathione derivatized microtiter plates, which are then combined with the test compound or the test compound and the nonadsorbed S-acyl fatty acid synthase thioesterase-like enzyme polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either an S-acyl fatty acid synthase thioesterase-like enzyme polypeptide (or polynucleotide) or a test compound can be immobilized utilizing conjugation of biotin and streptavidin. Biotinylated S-acyl fatty acid synthase thioesterase-like enzyme polypeptides (or polynucleotides) or test compounds can be prepared from biotinNHS(Nhydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to an S-acyl fatty acid synthase thioesterase-like enzyme polypeptide, polynucleotide, or a test compound, but which do not interfere with a desired binding site, such as the active site of the S-acyl fatty acid synthase thioesterase-like enzyme polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the S-acyl fatty acid synthase thioesterase-like enzyme polypeptide or test compound, enzyme-linked assays which rely on detecting an activity of the S-acyl fatty acid synthase thioesterase-like enzyme polypeptide, and SDS gel electrophoresis under non-reducing conditions.

Screening for test compounds which bind to an S-acyl fatty acid synthase thioesterase-like enzyme polypeptide or polynucleotide also can be carried out in an intact cell. Any cell which comprises an S-acyl fatty acid synthase thioesterase-like enzyme polypeptide or polynucleotide can be used in a cell-based assay system. An S-acyl fatty acid synthase thioesterase-like enzyme polynucleotide can be naturally occurring in the cell or can be introduced using techniques such as those described above. Binding of the test compound to an S-acyl fatty acid synthase thioesterase-like enzyme polypeptide or polynucleotide is determined as described above.

Enzyme Assays

Test compounds can be tested for the ability to increase or decrease the S-acyl fatty acid synthase thioesterase activity of a human S-acyl fatty acid synthase thioesterase-like enzyme polypeptide. S-acyl fatty acid synthase thioesterase activity can be measured, for example, as described in U.S. Pat. No. 4,529,693 (see Example 2). Enzyme assays can be carried out after contacting either a purified S-acyl fatty acid synthase thioesterase-like enzyme polypeptide, a cell membrane preparation, or an intact cell with a test compound. A test compound which decreases an S-acyl fatty acid synthase thioesterase activity of an S-acyl fatty acid synthase thioesterase-like enzyme polypeptide by at least about 10, preferably about 50, more preferably about 75, 90, or 100% is identified as a potential therapeutic agent for decreasing S-acyl fatty acid synthase thioesterase-like enzyme activity. A test compound which increases an S-acyl fatty acid synthase thioesterase activity of a human S-acyl fatty acid synthase thioesterase-like enzyme polypeptide by at least about 10, preferably about 50, more preferably about 75, 90, or 100% is identified as a potential therapeutic agent for increasing human S-acyl fatty acid synthase thioesterase-like enzyme activity.

Gene Expression

In another embodiment, test compounds which increase or decrease S-acyl fatty acid synthase thioesterase-like enzyme gene expression are identified. An S-acyl fatty acid synthase thioesterase-like enzyme polynucleotide is contacted with a test compound, and the expression of an RNA or polypeptide product of the S-acyl fatty acid synthase thioesterase-like enzyme polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of S-acyl fatty acid synthase thioesterase-like enzyme mRNA or polypeptide expression in the cells can be determined by methods well known in the art for detecting mRNA or polypeptide. Either qualitative or quantitative methods can be used. The presence of polypeptide products of an S-acyl fatty acid synthase thioesterase-like enzyme polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into an S-acyl fatty acid synthase thioesterase-like enzyme polypeptide.

Such screening can be carried out either in a cell-free assay system or in an intact cell. Any cell which expresses an S-acyl fatty acid synthase thioesterase-like enzyme polynucleotide can be used in a cell-based assay system. The S-acyl fatty acid synthase thioesterase-like enzyme polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions which can be administered to a patient to achieve a therapeutic effect. Pharmaceutical compositions of the invention can comprise, for example, an S-acyl fatty acid synthase thioesterase-like enzyme polypeptide, S-acyl fatty acid synthase thioesterase-like enzyme polynucleotide, ribozymes or antisense oligonucleotides, antibodies which specifically bind to an S-acyl fatty acid synthase thioesterase-like enzyme polypeptide, or mimetics, agonists, antagonists, or inhibitors of an S-acyl fatty acid synthase thioesterase-like enzyme polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push fit capsules made of gelatin, as well as soft, sealed capsules made of gelatin and a coating, such as glycerol or sorbitol. Push fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 150 mM histidine, 0.1%2% sucrose, and 27% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Various fatty acids and dietary triglycerides are involved in the complex regulation of lipid metabolism. More recently accumulated evidence indicates that medium chain fatty acids are generally undesirable in humans, since medium chain fatty acids contribute to raising low density lipoprotein (LDL) blood cholesterol level (3, 4, 5). See U.S. Pat. No. 5,981,575. High levels of LDL blood cholesterol in turn have been implicated as associated with a number of conditions and diseases, including obesity, diabetes, hyperlipidemia, and cardiovascular disease. The enzyme S-acyl fatty acid synthase thioesterase contributes to the regulation of LDL levels. Compounds directed to the regulation of S-acyl fatty acid synthase thioesterase may therefore prove useful as therapeutic agents for diseases such as obesity, diabetes, hyperlipidemia, and cardiovascular disease.

The metabolism of fat plays a critical role in obesity and is influenced by numerous factors, including lipid metabolism and the many enzymatic activities that constitute lipid metabolism, including that of S-acyl fatty acid synthase thioesterase. Obesity is associated with important medical morbidities and an increase in mortality. Obesity and overweight are defined as an excess of body fat relative to lean body mass. An increase in caloric intake or a decrease in energy expenditure or both can bring about this imbalance leading to surplus energy being stored as fat. The causes of obesity are poorly understood and may be due to genetic factors, environmental factors or a combination of the two to cause a positive energy balance. In contrast, anorexia and cachexia are characterized by an imbalance in energy intake versus energy expenditure leading to a negative energy balance and weight loss. Agents that either increase energy expenditure and/or decrease energy intake, absorption or storage would be useful for treating obesity, overweight, and associated co-morbidities. Agents that either increase energy intake and/or decrease energy expenditure or increase the amount of lean tissue would be useful for treating cachexia, anorexia and wasting disorders.

The S-acyl fatty acid synthase thioesterase gene, translated proteins and agents which modulate the S-acyl fatty acid synthase thioesterase gene or portions of the gene or its products are useful candidates for treating obesity, overweight, anorexia, cachexia, wasting disorders, appetite suppression, appetite enhancement, increases or decreases in satiety, modulation of body weight, and/or other eating disorders such as bulimia. Also the S-acyl fatty acid synthase thioesterase gene, translated proteins and agents which modulate the S-acyl fatty acid synthase thioesterase gene or portions of the gene or its products may prove useful for treating obesity/overweight-associated co-morbidities including type 2 diabetes, hyperlipidemia, and cardiovascular disease.

Diabetes mellitus is a common metabolic disorder characterized by an abnormal elevation in blood glucose, alterations in lipids and abnormalities (complications) in the cardiovascular system, eye, kidney and nervous system. Diabetes is divided into two separate diseases: type 1 diabetes juvenile onset), which results from a loss of cells which make and secrete insulin, and type 2 diabetes (adult onset), which is caused by a defect in insulin secretion and a defect in insulin action.

Type II diabetes is the most common of the two diabetic conditions (6% of the population). The defect in insulin secretion is an important cause of the diabetic condition and results from an inability of the beta cell to properly detect and respond to rises in blood glucose levels with insulin release. Therapies that increase the response by the beta cell to glucose would offer an important new treatment for this disease.

The defect in insulin action in Type II diabetic subjects is a target for therapeutic intervention. Agents that increase the activity of the insulin receptor in muscle, liver, and fat will cause a decrease in blood glucose and a normalization of plasma lipids. The normalization of plasma lipids can also be targeted by agents that regulate lipid metabolism. Therapies that can directly effect the various enzyme systems involved in lipid metabolism, including S-acyl fatty acid synthase thioesterase and S-acyl fatty acid synthase, can potentially generate an insulin-like effect and therefore a produce beneficial outcome.

In addition to therapeutic implications for S-acyl fatty acid synthase thioesterase for obesity and diabetes, regulation of the enzyme is likely to be beneficial in treating cardiovascular diseases. These diseases Cardiovascular diseases include the following disorders of the heart and the vascular system: congestive heart failure, myocardial infarction, ischemic diseases of the heart, all kinds of atrial and ventricular arrhythmias, hypertensive vascular diseases and peripheral vascular diseases.

Heart failure is defined as a pathophysiologic state in which an abnormality of cardiac function is responsible for the failure of the heart to pump blood at a rate commensurate with the requirement of the metabolizing tissue. It includes all forms of pumping failure such as high output and low output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications. Ischemic diseases are conditions in which the coronary flow is restricted resulting in an perfusion which is inadequate to meet the myocardial requirement for oxygen. This group of diseases include stable angina, unstable angina and asymptomatic ischemia.

Arrhythmias include all forms of atrial and ventricular tachyarrhythmias (atrial tachycardia, atrial flutter, atrial fibrillation, atrioventricular reentrant tachycardia, pre-excitation syndrome, ventricular tachycardia, ventricular flutter, ventricular fibrillation) as well as bradycardic forms of arrhythmias.

Hypertensive vascular diseases include primary as well as all kinds of secondary arterial hypertension (renal, endocrine, neurogenic, others). The genes may be used as drug targets for the treatment of hypertension as well as for the prevention of all complications. Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon and venous disorders.

Cardiovascular disease has been linked to elevated serum cholesterol by a large amount of evidence. For example, atherosclerosis is a slowly progressive disease characterized by the accumulation of cholesterol within the arterial wall. Compelling evidence supports the concept that lipids deposited in atherosclerotic lesions are derived primarily from plasma LDL; thus, LDLs have popularly become known as the "bad" cholesterol. Thus, the enzymes that contribute to LDL metabolism, such as S-acyl fatty acid synthase thioesterase, can serve as potential therapeutic targets for the above-described cardiovascular diseases.

As detailed above, obesity, diabetes, and cardiovascular disease are associated with lipid metabolism. The many fatty acids and dietary triglycerides that are involved in the regulation of lipid metabolism include medium chain fatty acids, which contribute to raising low density lipoprotein (LDL) blood cholesterol levels. The regulation of LDL levels is affected by the amount of medium chain fatty acids that are produced by the fatty acid synthase complex. In that complex, the specificity of fatty acid synthase is shifted from long chain fatty acids to medium chain by modification of the enzyme by another enzyme, S-acyl fatty acid synthase thioesterase, as evidenced in studies of S-acyl fatty acid synthase thioesterase from rats (1) and transgenic plants (2). By blocking the activity of S-acyl fatty acid synthase thioesterase, general LDL levels may be lowered. Inhibition of an S-acyl fatty acid synthase thioesterase-like activity therefore provides a wide range of potential therapeutic applications.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or an S-acyl fatty acid synthase thioesterase-like enzyme polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above described screening assays for treatments as described herein.

A reagent which affects S-acyl fatty acid synthase thioesterase-like enzyme activity can be administered to a human cell, either in vitro or in vivo, to reduce S-acyl fatty acid synthase thioesterase-like enzyme activity. The reagent preferably binds to an expression product of a human S-acyl fatty acid synthase thioesterase-like enzyme gene. If the expression product is a protein, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about 106 cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient which increases or decreases S-acyl fatty acid synthase thioesterase-like enzyme activity relative to the S-acyl fatty acid synthase thioesterase-like enzyme activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of an S-acyl fatty acid synthase thioesterase-like enzyme gene or the activity of an S-acyl fatty acid synthase thioesterase-like enzyme polypeptide by at least about 10, preferably about 50, more preferably about 75, 90, or 100% relative to the absence of the reagent. The effectiveness of the mechanism chosen to decrease the level of expression of an S-acyl fatty acid synthase thioesterase-like enzyme gene or the activity of an S-acyl fatty acid synthase thioesterase-like enzyme polypeptide can be assessed using methods well known in the art, such as hybridization of nucleotide probes to S-acyl fatty acid synthase thioesterase-like enzyme-specific mRNA, quantitative RT-PCR, immunologic detection of an S-acyl fatty acid synthase thioesterase-like enzyme polypeptide, or measurement of S-acyl fatty acid synthase thioesterase-like enzyme activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human S-acyl fatty acid synthase thioesterase-like enzyme also can be used in diagnostic assays for detecting diseases and abnormalities or susceptibility to diseases and abnormalities related to the presence of mutations in the nucleic acid sequences which encode the enzyme. For example, differences can be determined between the cDNA or genomic sequence encoding S-acyl fatty acid synthase thioesterase-like enzyme in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S 1 protection or the chemical cleavage method (e.g., Cotton et al., *Proc. Natl. Acad. Sci. USA* 85, 43974401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel electrophoresis and DNA sequencing, mutations can also be detected by in situ analysis.

Altered levels of an S-acyl fatty acid synthase thioesterase-like enzyme also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents and patent applications cited in this disclosure are expressly incorporated herein by reference. The above disclosure generally describes the present invention. A more complete understanding can be obtained by reference to the following specific examples which are provided for purposes of illustration only and are not intended to limit the scope of the invention.

EXAMPLE 1

Detection of S-acyl Fatty Acid Synthase Thioesterase-like enzyme Activity

The polynucleotide of SEQ ID NO: 12 is inserted into the expression vector pCEV4, and the expression vector pCEV4-S-acyl fatty acid synthase thioesterase-like enzyme polypeptide obtained is transfected into human embryonic kidney 293 cells. From these cells, extracts are obtained. S-acyl fatty acid synthase thioesterase-like enzyme activity is measured spectrophotometrically using Ellman's reagent (5,5'-dithiobis(2-nitrobenzoic acid)) as described previously (Smith, *Methods Enzymol.* 71, 181–88, 1981) with 0.125 µg cell extract in a volume of 0.5 ml. A radiochemical assay contains [1–14C]palmitoyl CoA (31,4 Ci/mol) in a volume of 0.1 ml. Incubation is at 25° C. The free 14C palmitic acid produced is extracted and assayed by liquid scintillation spectrometry. It is shown that the polypeptide of SEQ ID NO: 2 has an S-acyl fatty acid synthase thioesterase-like enzyme activity.

EXAMPLE 2

Expression of Recombinant Human S-acyl Fatty Acid Synthase Thioesterase-like Enzyme The *Pichia pastoris* expression vector pPICZB (Invitrogen, San Diego, Calif.) is used to produce large quantities of recombinant human S-acyl fatty acid synthase thioesterase-like polypeptides in yeast. The S-acyl fatty acid synthase thioesterase-like enzyme-encoding DNA sequence is derived from SEQ ID NO:12. Before insertion into vector pPICZB, the DNA sequence is modified by well known methods in such a way that it contains at its 5' end an initiation codon and at its 3' end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris,* driven by a yeast promoter. The resulting pPICZ/mdHis6 vector is used to transform the yeast.

The yeast is cultivated under usual conditions in 5 liter shake flasks and the recombinantly produced protein isolated from the culture by affinity chromatography (NiNTA Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human S-acyl fatty acid synthase thioesterase-like enzyme polypeptide is obtained.

EXAMPLE 3

Identification of a Test Compound that Decreases S-acyl Fatty Acid Synthase Thioesterase-like Activity S-acyl fatty acid synthase thioesterase-like activity can be assayed using cellular extracts from human breast cell lines, such as the cell line SKBr3. Test compounds from a small molecule library can be assayed for their ability to regulate S-acyl fatty acid synthase thioesterase-like activity by contacting human breast cell line extracts with the test compounds. Control extracts, in the absence of a test compound, also are assayed. S-acyl fatty acid synthase thioesterase-like activity can be measured using radiochemically labeled substrate, such as $^{14}$C-fatty acyl fatty acid synthase, as described in U.S. Pat. No. 4,529,693.

A test compound which decreases S-acyl fatty acid synthase thioesterase-like activity of an enzyme relative to the control preparation by at least 20% is identified as an S-acyl fatty acid synthase thioesterase-like enzyme inhibitor.

EXAMPLE 4

Identification of Test Compounds that Bind to S-acyl Fatty Acid Synthase Thioesterase-like Enzyme Polypeptides Purified S-acyl fatty acid synthase thioesterase-like enzyme polypeptides comprising a glutathione-S-transferase protein and absorbed onto glutathione-derivatized wells of 96-well microtiter plates are contacted with test compounds from a small molecule library at pH 7.0 in a physiological buffer solution. S-acyl fatty acid synthase thioesterase-like enzyme polypeptides comprise the amino acid sequence shown in SEQ ID NO:2. The test compounds comprise a fluorescent tag. The samples are incubated for 5 minutes to one hour. Control samples are incubated in the absence of a test compound.

The buffer solution containing the test compounds is washed from the wells. Binding of a test compound to an S-acyl fatty acid synthase thioesterase-like enzyme polypeptide is detected by fluorescence measurements of the contents of the wells. A test compound which increases the fluorescence in a well by at least 15% relative to fluorescence of a well in which a test compound is not incubated is identified as a compound which binds to an S-acyl fatty acid synthase thioesterase-like enzyme polypeptide.

EXAMPLE 5

Identification of a Test Compound which Decreases S-acyl Fatty Acid Synthase Thioesterase-like Enzyme Gene Expression A test compound is administered to a culture of human cells transfected with an S-acyl fatty acid synthase thioesterase-like enzyme expression construct and incubated at 37° C. for 10 to 45 minutes. A culture of the same type of cells which have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled S-acyl fatty acid synthase thioesterase-like enzyme-specific probe at 65° C. in Express-hyb (CLONTECH). The probe comprises at least 11 contiguous nucleotides selected from the complement of SEQ ID NO: 1. A test compound which decreases the S-acyl fatty acid synthase thioesterase-like enzyme-specific signal relative to the signal obtained in the absence of the test compound is identified as an inhibitor of S-acyl fatty acid synthase thioesterase-like enzyme gene expression.

EXAMPLE 6

Treatment of Hyperlipidemia with a Reagent which Specifically Binds to an S-acyl Fatty Acid Synthase Thioesterase-like Enzyme Gene Product Synthesis of antisense S-acyl fatty acid synthase thioesterase-like enzyme oligonucleotides comprising at least 11 contiguous nucleotides selected from the complement of SEQ ID NO:1 is performed on a Pharmacia Gene Assembler series synthesizer using the phosphoramidite procedure (Uhlmann et al., *Chem. Rev.* 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the Limulus Amebocyte Assay (Bang, *Biol. Bull.* (Woods Hole, Mass.) 105, 361362, 1953).

The antisense oligonucleotides are administered to a patient with hyperlipidemia. The severity of the patient's hyperlipidemia is decreased.

EXAMPLE 7

Tissue-specific Expression of s-acyl Fatty Acid Synthase Thioesterase-Like Enzyme The qualitative expression pattern of S-acyl fatty acid synthase thioesterase-like enzyme in various tissues was determined by Reverse Transcription-Polymerase Chain Reaction (RT-PCR). The results are shown in Table 1 and in FIG. 3.

TABLE 1

| Normal Tissue | RT-PCR |
| --- | --- |
| Adipose Sub. | + |
| Adipose Mes. | + |
| Brain | + |
| Colon | − |
| Heart | + |
| Hypothalamus | − |
| Islet Library | − |
| Kidney | + |
| Liver | − |
| Lung | + |
| Mammary Gland | + |
| Pancreas | − |
| Placenta | + |
| Prostate | − |
| Skeletal Muscle | + |
| Spleen | + |

EXAMPLE 8

Tissue-specific Expression of s-acyl Fatty Acid Synthase Thioesterase-like Enzyme To demonstrate that S-acyl fatty acid synthase thioesterase-like enzyme is involved in the disease process of diabetes, the following whole body panel is screened to show predominant or relatively high expression: subcutaneous and mesenteric adipose tissue, adrenal gland, bone marrow, brain, colon, fetal brain, heart, hypothalamus, kidney, liver, lung, mammary gland, pancreas, placenta, prostate, salivary gland, skeletal muscle, small intestine, spleen, stomach, testis, thymus, thyroid, trachea, and uterus. Human islet cells and an islet cell library also are tested. As a final step, the expression of S-acyl fatty acid synthase thioesterase-like enzyme in cells derived from normal individuals with the expression of cells derived from diabetic individuals is compared.

To demonstrate that S-acyl fatty acid synthase thioesterase-like enzyme is involved in the disease process of obesity, expression is determined in the following tissues: subcutaneous adipose tissue, mesenteric adipose tissue, adrenal gland, bone marrow, brain (cerebellum, spinal cord, cerebral cortex, caudate, medulla, substantia nigra, and putamen), colon, fetal brain, heart, kidney, liver, lung, mammary gland, pancreas, placenta, prostate, salivary gland, skeletal muscle small intestine, spleen, stomach, testes, thymus, thyroid trachea, and uterus. Neuroblastoma cell lines SK-Nr-Be (2), Hr, Sk-N-As, HTB-10, IMR-32, SNSY-5Y, T3, SK-N-D2, D283, DAOY, CHP-2, U87MG, BE(2)C, T986, KANTS, M059K, CHP234, C6 (rat), SK-N-Fl, SK-PU-DW, PFSK-1, BE(2)M17, and MCIXC also are tested for S-acyl fatty acid synthase thioesterase-like enzyme expression. As a final step, the expression of S-acyl fatty acid synthase thioesterase-like enzyme in cells derived from normal individuals with the expression of cells derived from obese individuals is compared.

Quantitative Expression Profiling.

Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'-3' endonuclease activity of Taq DNA polymerase and a fluorescent dye released in the medium (Holland et al., *Proc. Natl. Acad. Sci. U.S.A.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA Extraction and cDNA Preparation.

Total RNA from the tissues listed above are used for expression quantification. RNAs labeled "from autopsy" were extracted from autoptic tissues with the TRIzol reagent (Life Technologies, MD) according to the manufacturer's protocol.

Fifty $\mu$g of each RNA are treated with DNase I for 1 hour at 37° C. in the following reaction mix: 0.2 U/$\mu$l RNase-free DNase I (Roche Diagnostics, Germany); 0.4 U/·l RNase inhibitor (PE Applied Biosystems, CA); 10 mM Tris-HCl pH 7.9; 10 mM $MgCl_2$; 50 mM NaCl; and 1 mM DTT.

After incubation, RNA is extracted once with 1 volume of phenol:chloroform:isoamyl alcohol (24:24:1) and once with chloroform, and precipitated with 1/10 volume of 3 M NaAcetate, pH5.2, and 2 volumes of ethanol.

Fifty $\mu$g of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, CA) according to the manufacturer's protocol. The final concentration of RNA in the reaction mix is 200 ng/·L. Reverse transcription is carried out with 2.5·M of random hexamer primers.

TaqMan Quantitative Analysis.

Specific primers and probe are designed according to the recommendations of PE Applied Biosystems; probes are labeled either with FAM (6-carboxy-fluorescein) or with TAMRA (6-carboxy-tetramethyl-rhodamine). Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, CA).

The assay reaction mix is as follows: IX final TaqMan Universal PCR Master Mix (from 2× stock) (PE Applied Biosystems, CA); 1× PDAR control—18S RNA (from 20× stock); 300 nM forward primer; 900 nM reverse primer; 200 nM probe; 10 ng cDNA; and water to 25 $\mu$l.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

EXAMPLE 9

Diabetes: In vivo Testing of Compounds/Target Validation

1. Glucose Production:

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

2. Insulin Sensitivity:

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

3. Insulin Secretion:

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

Compounds that enhance insulin secretion from the pancreas will increase plasma insulin levels and improve the disappearance of plasma glucose following the administration of a glucose load. When measuring insulin levels, test compounds which regulate pristanoyl-CoA oxidase-like enzyme are administered by different routes (p.o., i.p., s.c., or i.v.) to overnight fasted normal rats or mice. At the appropriate time an intravenous glucose load (0.4 g/kg) is given, blood is collected one minute later. Plasma insulin levels are determined. Test compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60, and 90 minutes and plasma glucose levels determined. Test compounds that increase insulin levels will decrease glucose levels and the area-under the glucose curve when compared to the vehicle-treated group given only glucose.

4. Glucose Production:

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

5. Insulin Sensitivity:

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

6. Insulin Secretion:

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

EXAMPLE 10 cDNA Cloning of S-acyl Fatty Acid Synthase Thioesterase-like Enzyme Short (Long) Polypeptides A PCR reaction was carried out with standard methods, using human placenta cDNA as template and primers which introduced an Nco I site at the 5' end and an Xho I site at the 3' end. Two closely migrating PCR products of approximately the predicted size (819 bp) were isolated and ligated into pCRII (Invitrogen). The resulting plasmids were sequenced. The polynucleotide and amino acid sequences of S-acyl fatty acid synthase thioesterase-like enzyme (short) are shown in SEQ ID NOS:13 and 14, respectively. The polynucleotide and amino acid sequences of S-acyl fatty acid synthase thioesterase-like enzyme (long) are shown in SEQ ID NOS:15 and 16, respectively. The alignments of the two proteins are shown in FIG. 4.

After sequence confirmation, pCRII-S-acyl fatty acid synthase thioesterase-like enzyme short (long) polypeptide ("CoolEST49") was used as a template to introduce an N-terminal 6× His tag for purification of the protein. The sense oligonucleotide 5'-GAT GGA ATT CCC ATG GAG CAT CAC CAT CAC CAT CAC ATG GAG AGA GGA GAC CAA CCT AAG AGA-3' (SEQ ID NO:17) was used with the antisense cloning oligonucleotide GAT CTC GAG CTA AAA ATT GGA TAT CGA TGA TAC TTC (SEQ ID NO: 18). The resulting PCR product was digested with Nco I and Xho I and ligated in pET-28a vector (Novagen), which had also been digested with Nco I and Xho I. After sequence confirmation, pET-28a-S-acyl fatty acid synthase thioesterase-like enzyme short polypeptide was transformed into BL21 (DE3) for expression.

EXAMPLE 11

Solubility, Purification and Activity of S-acyl Fatty Acid Synthase Thioesterase-like Enzyme Short (Long) Polypeptides Solubility Study Procedure:

A solubility test was essentially performed according to the instructions of the manufacturer (The QIAEPRESSIONIST, A HANDBOOK FOR HIGH-LEVEL EXPRESSION AND PURIFICATION OF 6× HIS-TAGGED PROTEINS; 4$^{th}$ ed., January 2000), using *E. coli* expressing His6-tagged S-acyl fatty acid synthase thioesterase-like enzyme short (long) polypeptide (plasmid pET28ahis49s1).

Result:

Solubility of S-acyl fatty acid synthase thioesterase-like enzyme short (long) polypeptide was approximately the same under all conditions tested, so a large-scale preparation was grown at 37° C.

Purification

Procedure:

Purification of the His6-tagged S-acyl fatty acid synthase thioesterase-like enzyme short (long) polypeptide was carried out according to the instructions of the manufacturer. Further purification of the S-acyl fatty acid synthase thioesterase-like enzyme short (long) polypeptide was attempted by use of anion exchange chromatography. Two S-acyl fatty acid synthase thioesterase-like enzyme short (long) polypeptide peaks eluted from the column.

Result:

Total protein yield was 5.4 mg (2 peaks combined).

Activity assay

Procedure:

Activity of both protein peaks was assayed using an optimized discontinuous assay format. Reaction mixture was 100 mM Tris (pH 8.0), 100 nM coolEST49,±0.1 mM palmitoyl CoA in a volume of 100 μL. The mixture was allowed to incubate at room temperature for 3 hours. After incubation, 150 μL of developer mixture (0.42 mM DTNB in 100 mM Tris) was added, and the absorbance at 412 nm was measured using a 96-well plate reader, using samples without palmitoyl CoA as blanks.

Result:

The protein purified from *E. coli* is active, but requires excessive protein in the assay. Also, turnover is 1% of human thioesterase II (compared to literature values).

| [Peak 1] (nM) | $A_{412}$ with substrate | $A_{412}$ without substrate | Background subtracted |
|---|---|---|---|
| 540 | 0.6202 | 0.102 | 0.5182 |
| 270 | 0.4974 | 0.0453 | 0.4521 |
| 135 | 0.2539 | 0.0287 | 0.2252 |

Solubility study

Procedure:

Efforts to solubilize S-acyl fatty acid synthase thioesterase-like enzyme short (long) polypeptide involved adding 10% glycerol or 50 mM betaine to growing cell cultures at the time of induction with 1 mm IPTG. These conditions were carried out at both 25° C. and 37° C. This was unsuccessful in increasing solubility of coolEST49, so low temperature and varying IPTG concentrations was tried. Cells were grown at 15° C. and induced with 10 μM, 100 μM, and 1 mM IPTG.

Result:

All attempts at solubilizing S-acyl fatty acid synthase thioesterase-like enzyme short (long) polypeptide in *E. coli* failed.

Repeat of purification

Procedure:

To purify more S-acyl fatty acid synthase thioesterase-like enzyme short (long) polypeptide to try to improve activity, cells were again grown using the previously mentioned conditions. This time, after the anion exchange chromatography step, a cation exchange chromatography step was attempted to purify sample further. Sample was lost at this stage.

Result:

No protein was obtained from this *E. coli* preparation.

Activity Assay/Inhibition

Procedure:

Activity of S-acyl fatty acid synthase thioesterase-like enzyme short (long) polypeptide from the anion exchange column was assayed and compared to that of the eluate from the Ni-NTA column step. An attempt was also made at inhibiting S-acyl fatty acid synthase thioesterase-like enzyme short (long) polypeptide with either DEPC (7 mM) or AEBSF (1 mM).

Figure 5:
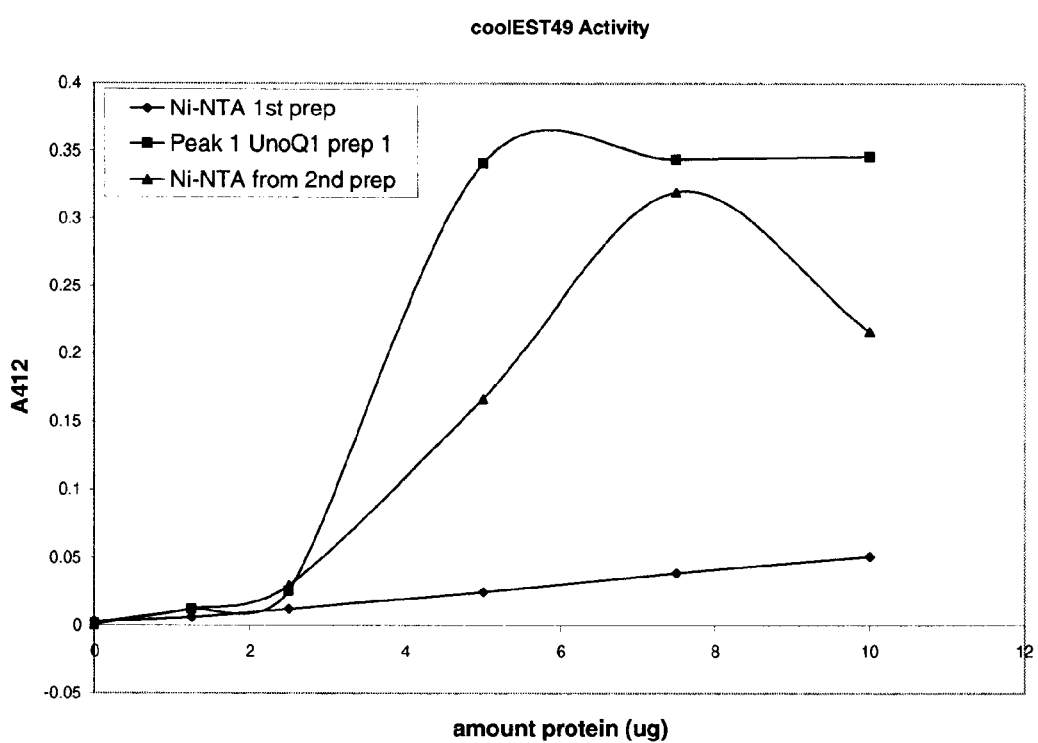
FIG. 5. Activity of S-acyl fatty acid synthase thioesterase-like enzyme short (long).
Figure 6:
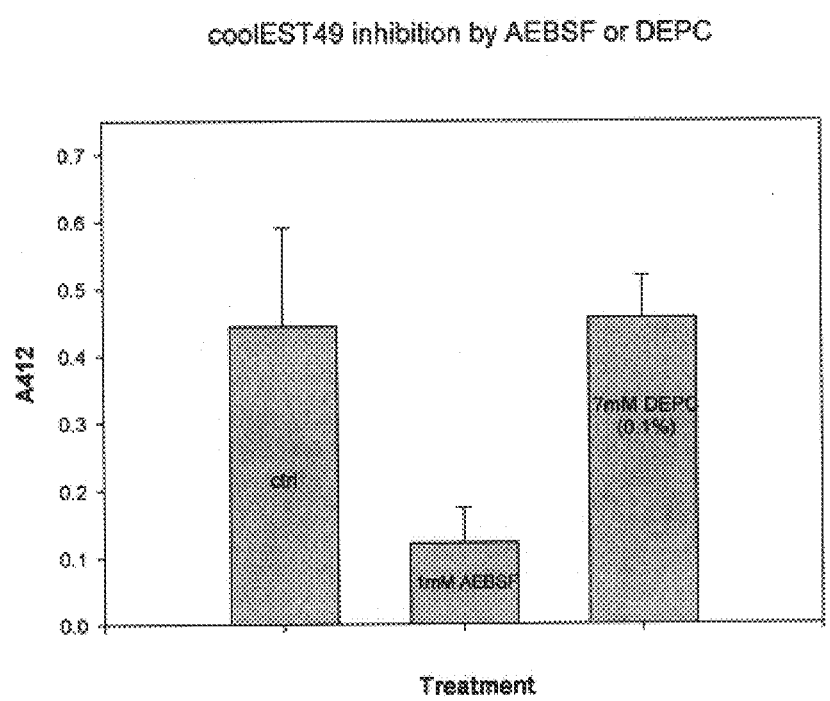
FIG. 6. Inhibition of S-acyl fatty acid synthase thioesterase-like enzyme short (long).

Result:

The activity of S-acyl fatty acid synthase thioesterase-like enzyme short (long) polypeptide from the anion exchange column of Prep 1 and the Ni-NTA column of Prep 2 showed a sigmoidal substrate/activity relationship. S-acyl fatty acid synthase thioesterase-like enzyme short (long) polypeptide activity was inhibited by 1 mM AEBSF, but not by 7 mM DEPC (FIGS. 5 and 6).

Purification from Baculovirus

Procedure:

Purification of the His6-tagged S-acyl fatty acid synthase thioesterase-like enzyme short (long) polypeptide was carried out essentially according to the instructions of the manufacturer.

Result:

Total protein yield from a 4 L Sf9 culture, grown to 48 hpi with an MOI of 5, was 52 mg; S-acyl fatty acid synthase thioesterase-like enzyme short (long) polypeptide purified to 75% in a single step.

Kinetics of Batch 1/Substrate Searching

Procedure:

A continuous assay format was used to get kinetic information on this preparation of S-acyl fatty acid synthase thioesterase-like enzyme short (long) polypeptide, using the same conditions as with the discontinuous assay, except with this format, developer was added to enzyme until a flat signal was achieved, then the reaction was started by the addition of substrate. Along with palmitoyl CoA, the other substrates assayed were acetyl CoA, octanoyl CoA, decanoyl CoA, and lauroyl CoA.

Result:

Using the continuous assay, the activity of S-acyl fatty acid synthase thioesterase-like enzyme short (long) polypeptide is linear in proportion to the amount of protein in the assay (up to 13 μg). This relationship of activity to protein amount was also observed in the crude lysates. Specific activity was 140.4 pmol/s/mg (using palmitoyl CoA as a substrate).

| Substrate | $k_{cat}$ (min$^{-1}$) | $K_m$ (μM) |
|---|---|---|
| Palmitoyl CoA | 1.0* | 5.1 |
| Lauroyl CoA | 1.0 | 76.7 |
| Decanoyl CoA | 2.8 | 856.1 |
| Octanoyl CoA | 6.9 | 12,400 |
| Acetyl CoA | immeasurable | immeasurable |

*units of activity are assigned with 1.0 being 23 mOD/min, using the assay conditions described

Purification of $2^{nd}$ Batch from Baculovirus

Procedure:

Purification of the His6-tagged S-acyl fatty acid synthase thioesterase-like enzyme short (long) polypeptide was carried out according to the instructions of the manufacturer.

Result:

Total protein yield was 49 mg; S-acyl fatty acid synthase thioesterase-like enzyme short (long) polypeptide purified to ~75% in a single step.

Test of Expression Under Different Growth Conditions

Procedure:

S-acyl fatty acid synthase thioesterase-like enzyme short (long) polypeptide was expressed in Sf9 and HiS cells, each with 48 and 72 hpi. All cells were lysed and the crude lysates were separated by SDS-polyacrylamide gel electrophoresis in an attempt to identify a growth condition in which more S-acyl fatty acid synthase thioesterase-like enzyme short (long) polypeptide was expressed. The crude lysate supernatants of cells with each of these growth conditions also were assayed for S-acyl fatty acid synthase thioesterase-like enzyme short (long) polypeptide activity using the assay described above.

Result:

None of the growth conditions resulted in a difference in either expression of S-acyl fatty acid synthase thioesterase-like enzyme short (long) polypeptide or its activity.

Kinetics of Batch 2 from Baculovirus

Procedure:

S-acyl fatty acid synthase thioesterase-like enzyme short (long) polypeptide activity was assayed in the continuous format as described.

Result:

This preparation of S-acyl fatty acid synthase thioesterase-like enzyme short (long) polypeptide had a specific activity of 179.8 pmol/s/mg (using palmitoyl CoA as a substrate) and a Km of 2.4 $\mu$M.

Purification of $3^{rd}$ Batch from Baculovirus

Procedure:

Purification of the His6-tagged S-acyl fatty acid synthase thioesterase-like enzyme short (long) polypeptide was carried out according to the instructions of the manufacturer.

Result:

Total protein yield was 20 mg; S-acyl fatty acid synthase thioesterase-like enzyme short (long) polypeptide purified to 75% in a single step.

Kinetics of Batch 3 from Baculovirus

Procedure:

S-acyl fatty acid synthase thioesterase-like enzyme short (long) polypeptide activity was assayed in the continuous format as described.

Result:

This preparation of S-acyl fatty acid synthase thioesterase-like enzyme short (long) polypeptide had a specific activity of 394.6 pmol/s/mg (using palmitoyl CoA as a substrate) and a $K_m$ of 5.1 $\mu$M.

Comparison of Continuous and Discontinuous Assay Format

Procedure:

S-acyl fatty acid synthase thioesterase-like enzyme short (long) polypeptide was incubated in the presence or absence of DTNB, and the $A_{412}$ was monitored until a baseline was achieved. Substrate (palmitoyl CoA) was then added to each incubation and was incubated for an additional 50 minutes. After this period of time, $A_{412}$ of each sample was compared to determine whether the pre-incubation of enzyme with DTNB inactivates the enzyme. Enzyme without substrate was used as a blank for the discontinuous assay.

Result:

DTNB, at the concentrations used in this assay format, appears to inactivate the enzyme by 60%.

| Format | Final $A_{412}$ (n = 2) |
| --- | --- |
| Continuous | 0.158 |
| Discontinuous | 0.391 |

96well Partition Assay Protocol Materials:

Palmitoyl coenzyme A, (Sigma, P9716)

[9,10(n)-$^3$]H-Palmitoyl coenzyme A,(Amersham, TRQ9329)

AEBSF, (Sigma, A8456)

Packard Picoplate, (Packard, 6005162)

Microscint CAT, (Packard, 6013661)

Phosphoric Acid, (Sigma, P6560)

Assay Buffer (AB): 50 mM HEPES pH7.5, 5 mM MgCl$_2$, 0.5 mg/ml BSA

| Stock | Dilution Factor | Working Conc. (Final Conc.) |
| --- | --- | --- |
| coolEST49, MW 31,000: | | |
| 41.9 uM* | 1/130 | 320 nM (32 nM F.C.) |
| *batch (11/2/00) 1.3 mg/ml, stored at $-20°$ C. | | |
| [9,10(n)-$^3$H]-Palmitoyl coenzyme A: | | |
| 19.6 uM* | 1/400 | 49 mN (4.9 nM F.C.) |
| *1 mCi/ml, 51 Ci/mmol in ethanol, stored at $-20°$ C. | | |
| Palmitoyl coenzyme A: | | |
| 20 mM* | 1/1000 | 20 uM (2 uM F.C.) |
| *made fresh in water, stored at $-20°$ C. | | |
| AEBSF(4-(2-Aminoethyl)Benzenesulfonyl Fluoride Hydrochloride): | | |
| 100 mM* | 1/5 2 | 0 mM (1 mM F.C.) |
| *made fresh in water, stored at $-20°$ C. | | |

Protocol:

Add 75 $\mu$L(or 79 uL**) Assay Buffer to plates.

Add 5 uL(or 1 uL) drug or 5%(or 70) % DMSO to A1-F1

Add 5 uL of AEBSF to G1-H1

Add 10 $\mu$L Palmitoyl CoA to all wells

Add 10 uL coolEST49 to all wells except D1-F1

Incubate 3–4 hrs

Stop with 25 uL 1% Phosphoric Acid

Wait 30 minutes

Add 150 uL Microscint CAT to all wells

Cover plates & Shake 1 hr

Let sit overnight on bench

Count, top detector only for Wallac Microbeta

**alternate (volumes) reflect 1 $\mu$L addition of test reagent/reference compound in 70% DMSO. The standard addition is 5 $\mu$L of 5% DMSO.

REFERENCES

1. Libertini L J, Smith S (1978) Purification and properties of a thioesterase from lactating rat mammary gland which modifies the product specificity of fatty acid synthetase. *J Biol Chem* 253(5):1393–401.
2. Dehesh K, Jones A, Knutzon D S, Voelker T A (1996) Production of high levels of 8:0 and 10:0 fatty acids in transgenic canola by overexpression of Ch FatB2, a thioesterase cDNA from Cuphea hookeriana. *Plant J* 9(2):167–72.
3. Tsai Y H, Park S, Kovacic J, Snook J T (1999) Mechanisms mediating lipoprotein responses to diets with medium-chain triglyceride and lauric acid. Lipids 34(9) :895–905.
4. Cater N B, Garg A (1997) Serum low-density lipoprotein cholesterol response to modification of saturated fat intake: recent insights *Curr Opin Lipidol* 8(6):332–6.
5. Mensink R P, Temme E H, Hornstra G (1994) Dietary saturated and trans fatty acids and lipoprotein metabolism. *Ann Med* 26(6):461–4.

What is claimed is:

1. A method of screening for agents that can inhibit thioesterase activity of a human S-acyl fatty acid synthase thioesterase-like enzyme, comprising the steps of:
   contacting a test compound with a polypeptide comprising the amino acid sequence shown in SEQ ID NO:2, wherein the polypeptide has a thioesterase activity; and
   detecting binding of the test compound to the polypeptide, wherein a test compound which binds to the polypeptide is identified as a potential agent for inhibiting thioesterase activity of the S-acyl fatty acid synthase thioesterase-like enzyme.

2. The method of claim 1 wherein the step of contacting is in a cell-free system.

3. The method of claim 1 wherein the polypeptide is labeled with a detectable label.

4. The method of claim 1 wherein the test compound comprises a detectable label.

5. The method of claim 1 wherein the test compound displaces a labeled ligand which is bound to the polypeptide.

6. The method of claim 1 wherein the polypeptide is bound to a solid support.

7. The method of claim 1 wherein the test compound is bound to a solid support.

8. A method of screening for agents which inhibit thioesterase activity of a human the S-acyl fatty acid synthase thioesterase-like enzyme, comprising the steps of:
   contacting a test compound with a polypeptide comprising the amino acid sequence shown in SEQ ID NO:2, wherein the polypeptide has a thioesterase activity; and
   detecting an activity of the polypeptide, wherein a test compound which inhibits the activity of the polypeptide is identified as a potential agent for inhibiting the activity of the human S-acyl fatty acid synthase thioesterase-like enzyme.

9. The method of claim 8 wherein the step of contacting is in a cell-free system.

10. A method of screening for agents that inhibit thioesterase activity of a human S-acyl fatty acid synthase thioesterase-like enzyme, comprising the steps of:
    contacting a test compound with a polypeptide product encoded by a polynucleotide which comprises the nucleotide sequence shown in SEQ ID NO:12; and
    detecting binding of the test compound to the product, wherein a test compound which binds to the product is identified as a potential agent for inhibiting thioesterase activity of the human S-acyl fatty acid synthase thioesterase like enzyme.

11. A method of screening for agents that can inhibit thioesterase activity of a human S-acyl fatty acid synthase thioesterase-like enzyme, comprising the steps of:
    contacting a test compound with a polypeptide comprising an amino acid sequence which is at least 98% identical to the amino acid sequence shown in SEQ ID NO:2, wherein the polypeptide has a thioesterase activity; and
    detecting binding of the test compound to the polypeptide, wherein a test compound which binds to the polypeptide is identified as a potential agent for inhibiting thioesterase activity of the S-acyl fatty acid synthase thioesterase-like enzyme.

12. A method of screening for agents that can inhibit thioesterase activity of a human S-acyl fatty acid synthase thioesterase-like enzyme, comprising the steps of:
    contacting a test compound with a polypeptide comprising an amino acid sequence which is at least 98% identical to the amino acid sequence shown in SEQ ID NO:2, wherein the polypeptide has a thioesterase activity; and
    detecting the thioesterase activity of the polypeptide, wherein a test compound which decreases the thioesterase activity of the polypeptide is identified as a potential inhibitor of the human S-acyl fatty acid synthase thioesterase-like enzyme.

* * * * *

SEQUENCE LISTING

<160> NUMBER OF SEQ ID NOS: 18

<210> SEQ ID NO 1
<211> LENGTH: 1432
<212> TYPE: DNA
<213> ORGANISM: Homo sapiens

<400> SEQUENCE: 1

| | | | | | |
|---|---|---|---|---|---|
| tttcagattg | tctgctcaga | gttcatctca | aagcctggca | aggattggag | aggtcaataa | 60 |
| gagtcagcgc | ctttaaaaag | aaatctactc | actcttctgt | gtgcataagg | ccgagcagag | 120 |
| gttcttcgtc | tcaagaggaa | ctgacttctg | ttgagcactc | aacacgccac | agagaccagc | 180 |
| catcttgcaa | cctcacctca | cagcatggag | agaggagacc | aacctaagag | aaccaggaat | 240 |
| gaaaacattt | tcaactgctt | atacaaaaac | cctgaggcaa | cttttaagct | gatttgcttt | 300 |
| ccctggatgg | gaggtggctc | cactcatttt | gccaaatggg | gccaagatac | tcatgatttg | 360 |
| ctggaagtgc | actccttaag | gcttcctgga | agagaaagca | gagttgaaga | acctcttgaa | 420 |
| aatgacatct | cccagttagt | tgatgaagtt | gtttgtgctc | tgcagccagt | catccaggat | 480 |
| aaaccatttg | catttttgg | ccacagtatg | ggatcctaca | ttgcttttag | gactgcacta | 540 |
| ggtctaaaag | aaaacaatca | accagaacca | ttgcatttat | ttttgtcaag | tgcaactcct | 600 |
| gtacattcaa | aggcctggca | tcgcattccc | aaagatgatg | aattgtcaga | gaacaaata | 660 |
| agtcattacc | ttatggaatt | tggaggcacc | cccaagcatt | tgctgaagc | caaggaattt | 720 |
| gtgaaacaat | gtagtcccat | cataagggca | gatctgaaca | ttgttagaag | ttgcacctct | 780 |
| aacgtaccat | ctaaggctgt | tcttcctgt | gacttgacat | gttttgttgg | atctgaagac | 840 |
| atagcaaagg | acatggaagc | ctggaaagat | gtaaccagtg | gaaatgctaa | aatttaccag | 900 |
| cttccagggg | gtcactttta | tcttctggat | cctgcgaacg | agaaattaat | caagaactac | 960 |
| ataatcaagt | gtctagaagt | atcatcgata | tccaattttt | agatattttc | cctttcactt | 1020 |
| ttaaaataat | caaagtaata | tcatactctt | ctcagttatt | cagatatagc | tcagttttat | 1080 |
| tcagattgga | aattacacat | tttctactgt | cagggagatt | cgttacataa | atatatttac | 1140 |
| gtatctgggg | acaaaggtca | agccagtaaa | gaatacttct | ggcagcactt | tgggaggcca | 1200 |
| aggcgggcgg | atcacgaggt | caggagatcg | agaccgtcct | ggctaacacc | gtgaaacccc | 1260 |
| atctctacta | aaaatacaca | aaattagctg | ggcgtggtgg | tgggcacctg | tagtcccagc | 1320 |
| tactcgggag | gctgaggcag | gagaatggtg | tgaacctggg | aggtggagct | tgcagtgaac | 1380 |
| cgagatcgct | ccactgcact | ccagcctggg | tgacagatcc | agactctgtc | tc | 1432 |

<210> SEQ ID NO 2
<211> LENGTH: 265
<212> TYPE: PRT
<213> ORGANISM: Homo sapiens

<400> SEQUENCE: 2

Met Glu Arg Gly Asp Gln Pro Lys Arg Thr Arg Asn Glu Asn Ile Phe
1               5                   10                  15

Asn Cys Leu Tyr Lys Asn Pro Glu Ala Thr Phe Lys Leu Ile Cys Phe
            20                  25                  30

Pro Trp Met Gly Gly Gly Ser Thr His Phe Ala Lys Trp Gly Gln Asp
        35                  40                  45

Thr His Asp Leu Leu Glu Val His Ser Leu Arg Leu Pro Gly Arg Glu
    50                  55                  60

```
Ser Arg Val Glu Glu Pro Leu Glu Asn Asp Ile Ser Gln Leu Val Asp
 65                  70                  75                  80

Glu Val Val Cys Ala Leu Gln Pro Val Ile Gln Asp Lys Pro Phe Ala
                 85                  90                  95

Phe Phe Gly His Ser Met Gly Ser Tyr Ile Ala Phe Arg Thr Ala Leu
                100                 105                 110

Gly Leu Lys Glu Asn Asn Gln Pro Glu Pro Leu His Leu Phe Leu Ser
            115                 120                 125

Ser Ala Thr Pro Val His Ser Lys Ala Trp His Arg Ile Pro Lys Asp
        130                 135                 140

Asp Glu Leu Ser Glu Glu Gln Ile Ser His Tyr Leu Met Glu Phe Gly
145                 150                 155                 160

Gly Thr Pro Lys His Phe Ala Glu Ala Lys Glu Phe Val Lys Gln Cys
                165                 170                 175

Ser Pro Ile Ile Arg Ala Asp Leu Asn Ile Val Arg Ser Cys Thr Ser
                180                 185                 190

Asn Val Pro Ser Lys Ala Val Leu Ser Cys Asp Leu Thr Cys Phe Val
            195                 200                 205

Gly Ser Glu Asp Ile Ala Lys Asp Met Glu Ala Trp Lys Asp Val Thr
        210                 215                 220

Ser Gly Asn Ala Lys Ile Tyr Gln Leu Pro Gly Gly His Phe Tyr Leu
225                 230                 235                 240

Leu Asp Pro Ala Asn Glu Lys Leu Ile Lys Asn Tyr Ile Ile Lys Cys
                245                 250                 255

Leu Glu Val Ser Ser Ile Ser Asn Phe
            260                 265

<210> SEQ ID NO 3
<211> LENGTH: 263
<212> TYPE: PRT
<213> ORGANISM: Rat

<400> SEQUENCE: 3

Met Glu Thr Ala Val Asn Ala Lys Ser Pro Arg Asn Glu Lys Val Leu
  1               5                  10                  15

Asn Cys Leu Tyr Gln Asn Pro Asp Ala Val Phe Lys Leu Ile Cys Phe
                 20                  25                  30

Pro Trp Ala Gly Gly Ser Ile His Phe Ala Lys Trp Gly Gln Lys
             35                  40                  45

Ile Asn Asp Ser Leu Glu Val His Ala Val Arg Leu Ala Gly Arg Glu
 50                  55                  60

Thr Arg Leu Gly Glu Pro Phe Ala Asn Asp Ile Tyr Gln Ile Ala Asp
 65                  70                  75                  80

Glu Ile Val Thr Ala Leu Leu Pro Ile Ile Gln Asp Lys Ala Phe Ala
                 85                  90                  95

Phe Phe Gly His Ser Phe Gly Ser Tyr Ile Ala Leu Ile Thr Ala Leu
                100                 105                 110

Leu Leu Lys Glu Lys Tyr Lys Met Glu Pro Leu His Ile Phe Val Ser
            115                 120                 125

Gly Ala Ser Ala Pro His Ser Thr Ser Arg Pro Gln Val Pro Asp Leu
        130                 135                 140

Asn Glu Leu Thr Glu Glu Gln Val Arg His His Leu Leu Asp Phe Gly
145                 150                 155                 160

Gly Thr Pro Lys His Leu Ile Glu Asp Gln Asp Val Leu Arg Met Phe
```

```
                    165                 170                 175
Ile Pro Leu Leu Lys Ala Asp Ala Gly Val Val Lys Lys Phe Ile Phe
                180                 185                 190

Asp Lys Pro Ser Lys Ala Leu Leu Ser Leu Asp Ile Thr Gly Phe Leu
            195                 200                 205

Gly Ser Glu Asp Thr Ile Lys Asp Ile Glu Gly Trp Gln Asp Leu Thr
    210                 215                 220

Ser Gly Lys Phe Asp Val His Met Leu Pro Gly Asp His Phe Tyr Leu
225                 230                 235                 240

Met Lys Pro Asp Asn Glu Asn Phe Ile Lys Asn Tyr Ile Ala Lys Cys
                245                 250                 255

Leu Glu Leu Ser Ser Leu Thr
            260

<210> SEQ ID NO 4
<211> LENGTH: 28
<212> TYPE: PRT
<213> ORGANISM: Artificial Sequence
<220> FEATURE:
<223> OTHER INFORMATION: pfamm[Th]ioesterase

<400> SEQUENCE: 4

Leu Pro Ala Gly Pro Arg Glu Gly Pro Tyr Leu Gly Ser Gly Gly Ala
 1               5                  10                  15

Glu Ala Leu Gly Leu Asp Pro Leu Trp Gly His Phe
            20                  25

<210> SEQ ID NO 5
<211> LENGTH: 773
<212> TYPE: DNA
<213> ORGANISM: Homo sapiens

<400> SEQUENCE: 5
tttttttttt tgatattact ttgattattt taaaagtgaa agggaaaata tctaaaaatt    60
ggatatcgat gatacttcta gacacttgat tatgtagttc ttgattaatt tctcgttcgc   120
aggatccaga agataaaagt gaccccctgg aagctggtaa attttagcat ttccactggt   180
tacatctttc caggcttcca tgtcctttgc tatgtcttca gatccaacaa acatgtcaa    240 gtcacaggaa agaacagcct tagatggtac gttagaggtg caacttctaa caatgttcag   300
atctgccctt atgatgggac tacattgttt cacaaattcc ttggcttcag caaaatgctt   360
gggggtgcct ccaaattcca taggtaatg acttatttgt tcttctgaca attcatcatc    420
tttgggaatg cgatgccagg cctttgaatg tacaggagtt gcacttgaca aaaataaatg   480
caatgggtct ggttgattgt tttcttttag acctagtgca gtcctaaaag caatgtagga   540
tcccatactg tggccaaaaa atgcaaatgg tttatcctgg atgactggct gcagagcaca   600
aacaacttcc tcaactaact gggagatggc ttttcaaga gttcttcaac tctgcttttt    660
ttccaggaag cccttaagag tgcacttcca ccaaattatg aatattttgg ccccatttgc   720
aaaaagaggg gagccacctc catccaggga aagcaaatca gctttaaagt ggc         773

<210> SEQ ID NO 6
<211> LENGTH: 508
<212> TYPE: DNA
<213> ORGANISM: Homo sapiens

<400> SEQUENCE: 6
tttactttga ttattttaaa agtgaaaggg aaaatatcta aaaattggat atcgatgata    60
```

```
cttctagaca cttgattatg tagttcttga ttaatttctc gttcgcagga tccagaagat    120
aaaagtgacc ccctggaagc tggtaaattt tagcatttcc actggttaca tctttccagg    180
cttccatgtc ctttgctatg tcttcagatc caacaaaaca tgtcaagtca caggaaagaa    240
cagccttaga tggtacgtta gaggtgcaac ttctaacaat gttcagatct gcccttatga    300
tgggactaca ttgtttcaca aattccttgg cttcagcaaa atgcttgggg gtgcctccaa    360
attccataag gtaatgactt atttgttctt ctgacaattc atcatctttg ggaatgcgat    420
gccaggcctt tgaatgtaca ggagttgcac ttgacaaaaa taaatgcaat ggttctggtt    480
gattgttttc ttttagacct agtgcagt                                       508
```

<210> SEQ ID NO 7
<211> LENGTH: 513
<212> TYPE: DNA
<213> ORGANISM: Homo sapiens

<400> SEQUENCE: 7

```
ttaactgaga agagtatgat attactttga ttatttaaa agtgaaaggg aaaatatcta     60
aaaattggat atcgatgata cttctagaca cttgattatg tagttcttga ttaatttctc    120
gttcgcagga tccagaagat aaaagtgacc ccctggaagc tggtaaattt tagcatttcc    180
actggttaca tctttccagg cttccatgtc ctttgctatg tcttcagatc caacaaaaca    240
tgtcaagtca caggaaagaa cagccttaga tggtacgtta gaggtgcaac ttctaacaat    300
gttcagatct gcccttatga tgggactaca ttgtttcaca aattccttgg cttcagcaaa    360
atgcttgggg gtgcctccaa attccataag gtaatgactt atttgttctt ctgacaattc    420
atcatctttg ggaatgcgat gccaggcctt tgaatgtaca ggagttgccc ttgacaaaaa    480
taaatgcaat ggttctggtt gattgttttc ttt                                 513
```

<210> SEQ ID NO 8
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 8

```
atgatattac tttgattatt ttaaaagtga agggaaaat atctaaaaat tggatatcga     60
tgatacttct agacacttga ttatgtagtt cttgattaat ttctcgttcg caggatccag    120
aagataaaag tgacccctg gaagctggta aattttagca tttccactgg ttacatcttt    180
ccaggcttcc atgtcctttg ctatgtcttc agatccaaca aaacatgtca agtcacagga    240
aagaacagcc ttagatggta cgttagaggt gcaacttcta acaatgttca gatctgccct    300
tatgatggga ctacattgtt tcacaaattc cttggcttca gcaaaatgct tggggggtgcc    360 tccaaattcc ataaggtaat gacttatttg ttcttctgac aattcatcat ctttgggaat    420
gcgatgccag gcctttgaat ggtacaggag ttgcacttga caaaaataaa tgccatggtt    480
cngggttgaa tggtttcctt tagacctagt gcagtcctaa aagccatgta ggatcccana    540
ctggggncca aaatgccatg ggttatccgg atgactggct gcagagncca aan           593
```

<210> SEQ ID NO 9
<211> LENGTH: 473
<212> TYPE: DNA

```
<213> ORGANISM: Homo sapiens

<400> SEQUENCE: 9
tttttttttt tgatattact ttgattattt taaaagtgaa agggaaaata tctaaaaatt      60
ggatatcgat gatacttcta gacacttgat tatgtagttc ttgattaatt tctcgttcgc     120
aggatccaga agataaaagt gacccctgg aagctggtaa attttagcat ttccactggt      180
tacatctttc caggcttcca tgtcctttgc tatgtcttca gatccaacaa acatgtcaa      240
gtcacaggaa agaacagcct tagatggtac gttagaggtg caacttctaa caatgttcag     300
atctgcccttt atgatgggac tacattgttt cacaaattcc ttggcttcag caaaatgctt     360
gggggtgcct ccaaattcca taaggtaatg acttatttgt tcttctgaca attcatcatc     420
tttgggaatg cgatgccagg cctttgaatg tacaggagtt gcacttgaca aaa            473

<210> SEQ ID NO 10
<211> LENGTH: 438
<212> TYPE: DNA
<213> ORGANISM: Homo sapiens

<400> SEQUENCE: 10 tttttatga tattactttg attattttaa aagtgaaagg gaaatatct aaaaattgga       60
tatcgatgat acttctagac acttgattat gtagttcttg attaatttct cgttcgcagg    120
atccagaaga taaagtgac ccctggaag ctggtaaatt ttagcatttc cactggttac      180
atctttccag gcttccatgt cctttgctat gtcttcagat ccaacaaaac atgtcaagtc    240
acaggaaaga acagccttag atggtacgtt agaggtgcaa cttctaacaa tgttcagatc    300
tgcccttatg atgggactac attgtttcac aaattccttg gcttcagcaa atgcttggg    360
ggtgcctcca aattccataa ggtaatgact tatttgttct tctgacaatt catcatcttt    420
gggaatgcga tgccaggc                                                  438

<210> SEQ ID NO 11
<211> LENGTH: 438
<212> TYPE: DNA
<213> ORGANISM: Homo sapiens

<400> SEQUENCE: 11 tttttatga tattactttg attattttaa aagtgaaagg gaaatatct aaaaattgga       60
tatcgatgat acttctagac acttgattat gtagttcttg attaatttct cgttcgcagg    120
atccagaaga taaagtgac ccctggaag ctggtaaatt ttagcatttc cactggttac      180
atctttccag gcttccatgt cctttgctat gtcttcagat ccaacaaaac atgtcaagtc    240
acaggaaaga acagccttag atggtacgtt agaggtgcaa cttctaacaa tgttcagatc    300
tgcccttatg atgggactac attgtttcac aaattccttg gcttcagcaa atgcttggg    360
ggtgcctcca aattccataa ggtaatgact tatttgttct tctgacaatt catcatcttt    420
gggaatgcga tgccaggc                                                  438

<210> SEQ ID NO 12
<211> LENGTH: 798
<212> TYPE: DNA
<213> ORGANISM: Homo sapiens

<400> SEQUENCE: 12
atggagagag gagaccaacc taagagaacc aggaatgaaa acattttcaa ctgcttatac     60
aaaaaccctg aggcaacttt taagctgatt tgctttccct ggatgggagg tggctccact    120
```

```
catttttgcca aatggggcca agatactcat gatttgctgg aagtgcactc cttaaggctt    180
cctggaagag aaagcagagt tgaagaacct cttgaaaatg acatctccca gttagttgat    240
gaagttgttt gtgctctgca gccagtcatc caggataaac catttgcatt ttttggccac    300
agtatgggat cctacattgc ttttaggact gcactaggtc taaaagaaaa caatcaacca    360
gaaccattgc atttattttt gtcaagtgca actcctgtac attcaaaggc ctggcatcgc    420
attcccaaag atgatgaatt gtcagaagaa caaataagtc attaccttat ggaatttgga    480
ggcaccccca agcatttttgc tgaagccaag gaatttgtga acaatgtag tcccatcata   540 agggcagatc tgaacattgt tagaagttgc acctctaacg taccatctaa ggctgttctt    600
tcctgtgact tgacatgttt tgttggatct gaagacatag caaaggacat ggaagcctgg    660
aaagatgtaa ccagtggaaa tgctaaaatt taccagcttc agggggtca cttttatctt    720 ctggatcctg cgaacgagaa attaatcaag aactacataa tcaagtgtct agaagtatca    780
tcgatatcca attttttag                                                   798
```

```
<210> SEQ ID NO 13
<211> LENGTH: 819
<212> TYPE: DNA
<213> ORGANISM: Homo sapiens

<400> SEQUENCE: 13
gatggaaatc ccatggagag aggagaccaa cctaagagaa ccaggaatga aaacattttc     60
aactgcttat acaaaaaccc tgaggcaact tttaagctga tttgctttcc ctggatggga   120
ggtggctcca ctcattttgc caaatggggc aagatactc atgatttgct ggaagtgcac    180
tccttaaggc ttcctggaag agaaagcaga gttgaagaac ctcttgaaaa tgacatctcc    240
cagttagttg atgaagttgt tgtgctctg cagccagtca tccaggataa accatttgca    300
ttttttggcc acagtatggg atcctacatt gcttttagga ctgcactagg tctgaaagaa   360
aacaatcaac cagaaccatt gcatttattt tgtcaagtg caactcctgt acattcaaag    420
gcctggcatc gcattcccaa agatgatgaa ttgtcagaag aacaaataag tcattacctt    480
atggaatttg gaggcacccc caagcatttt gctgaagcca aggaatttgt gaacaatgt    540 agtcccatca taagggcaga tctgaacatt gttagaagtt gcacctctaa cgtaccatct    600
aaggctgttc tttcctgtga cttgacatgt tttgttggat ctgaagacat agcaaaggac    660
atggaagcct ggaaagatgt aaccagtgga atgctaaaa tttaccagct tccagggggt   720
cacttttatc ttctggatcc tgcgaacgag aaattaatca gaactacat aatcaagtgt   780 ctagaagtat catcgatatc caatttttag ctcgagatc                            819
```

```
<210> SEQ ID NO 14
<211> LENGTH: 265
<212> TYPE: PRT
<213> ORGANISM: Homo sapiens

<400> SEQUENCE: 14

Met Glu Arg Gly Asp Gln Pro Lys Arg Thr Arg Asn Glu Asn Ile Phe
  1               5                  10                  15

Asn Cys Leu Tyr Lys Asn Pro Glu Ala Thr Phe Lys Leu Ile Cys Phe
                 20                  25                  30

Pro Trp Met Gly Gly Ser Thr His Phe Ala Lys Trp Gly Gln Asp
             35                  40                  45

Thr His Asp Leu Leu Glu Val His Ser Leu Arg Leu Pro Gly Arg Glu
```

```
                50                  55                  60
Ser Arg Val Glu Glu Pro Leu Glu Asn Asp Ile Ser Gln Leu Val Asp
 65                  70                  75                  80

Glu Val Val Cys Ala Leu Gln Pro Val Ile Gln Asp Lys Pro Phe Ala
                 85                  90                  95

Phe Phe Gly His Ser Met Gly Ser Tyr Ile Ala Phe Arg Thr Ala Leu
            100                 105                 110

Gly Leu Lys Glu Asn Asn Gln Pro Glu Pro Leu His Leu Phe Leu Ser
            115                 120                 125

Ser Ala Thr Pro Val His Ser Lys Ala Trp His Arg Ile Pro Lys Asp
        130                 135                 140

Asp Glu Leu Ser Glu Glu Gln Ile Ser His Tyr Leu Met Glu Phe Gly
145                 150                 155                 160

Gly Thr Pro Lys His Phe Ala Glu Ala Lys Glu Phe Val Lys Gln Cys
                165                 170                 175

Ser Pro Ile Ile Arg Ala Asp Leu Asn Ile Val Arg Ser Cys Thr Ser
            180                 185                 190

Asn Val Pro Ser Lys Ala Val Leu Ser Cys Asp Leu Thr Cys Phe Val
            195                 200                 205

Gly Ser Glu Asp Ile Ala Lys Asp Met Glu Ala Trp Lys Asp Val Thr
        210                 215                 220

Ser Gly Asn Ala Lys Ile Tyr Gln Leu Pro Gly Gly His Phe Tyr Leu
225                 230                 235                 240

Leu Asp Pro Ala Asn Glu Lys Leu Ile Lys Asn Tyr Ile Ile Lys Cys
                245                 250                 255

Leu Glu Val Ser Ser Ile Ser Asn Phe
            260                 265

<210> SEQ ID NO 15
<211> LENGTH: 978
<212> TYPE: DNA
<213> ORGANISM: Homo sapiens

<400> SEQUENCE: 15
gatggaaatc ccatggagag aggagaccaa cctaagagaa ccaggaatga aaacattttc      60
aactgcttat acaaaaaccc tgaggcaact tttaagctga tttgctttcc ctggatggga     120
ggtggctcca ctcattttgc caaatggggc aagatactc atgatttgct ggaagagaca      180
gcatctcacc atgttgccaa ggctggtctc aaactccggc gctcaagtga tcctcctgct     240
tcagcctacc atgtgctgg cgtgagccac cgtaggcgtg agccaccgtc cctggccaaa      300
attcttggtc tattctggat tctaattttt tttatgcact ccttaaggct tcctggaaga     360
gaaagcagag ttgaagaacc tcttgaaaat gacatctccc agttagttga tgaagttgtt     420
tgtgctctgc agccagtcat ccaggataaa ccatttgcat tttttggcca cagtatggga    480
tcctacattg cttttaggac tgcactaggt ctgaaagaaa acaatcaacc agaaccattg     540
catttatttt tgtcaagtgc aactcctgta cattcaaagg cctggcatcg cattcccaaa    600
gatgatgaat tgtcagaaga acaaataagt cattacctta tggaatttgg aggcaccccc    660
aagcattttg ctgaagccaa ggaatttgtg aaacaatgta gtcccatcat aagggcagat    720
ctgaacattg ttagaagttg cacctctaac gtaccatcta aggctgttct ttcctgtgac    780
ttgacatgtt ttgttggatc tgaagacata gcaaaggaca tggaagcctg aaagatgta    840 accagtggaa atgctaaaat ttaccagctt ccaggggtc acttttatct tctggatcct     900
```

```
gcgaacgaga aattaatcaa gaactacata atcaagtgtc tagaagtatc atcgatatcc    960
aatttttagc tcgagatc                                                  978
```

<210> SEQ ID NO 16
<211> LENGTH: 318
<212> TYPE: PRT
<213> ORGANISM: Homo sapiens

<400> SEQUENCE: 16

```
Met Glu Arg Gly Asp Gln Pro Lys Arg Thr Arg Asn Glu Asn Ile Phe
 1               5                  10                  15

Asn Cys Leu Tyr Lys Asn Pro Glu Ala Thr Phe Lys Leu Ile Cys Phe
            20                  25                  30

Pro Trp Met Gly Gly Ser Thr His Phe Ala Lys Trp Gly Gln Asp
        35                  40                  45

Thr His Asp Leu Leu Glu Glu Thr Ala Ser His Val Ala Lys Ala
    50                  55                  60

Gly Leu Lys Leu Arg Arg Ser Ser Asp Pro Ala Ser Ala Tyr Pro
65                  70                  75                  80

Cys Ala Gly Val Ser His Arg Arg Glu Pro Pro Cys Leu Ala Lys
                85                  90                  95

Ile Leu Gly Leu Phe Trp Ile Leu Ile Phe Phe Met His Ser Leu Arg
            100                 105                 110

Leu Pro Gly Arg Glu Ser Arg Val Glu Glu Pro Leu Glu Asn Asp Ile
        115                 120                 125

Ser Gln Leu Val Asp Glu Val Val Cys Ala Leu Gln Pro Val Ile Gln
    130                 135                 140

Asp Lys Pro Phe Ala Phe Gly His Ser Met Gly Ser Tyr Ile Ala
145                 150                 155                 160

Phe Arg Thr Ala Leu Gly Leu Lys Glu Asn Asn Gln Pro Glu Pro Leu
                165                 170                 175

His Leu Phe Leu Ser Ser Ala Thr Pro Val His Ser Lys Ala Trp His
            180                 185                 190

Arg Ile Pro Lys Asp Asp Glu Leu Ser Glu Glu Gln Ile Ser His Tyr
        195                 200                 205

Leu Met Glu Phe Gly Gly Thr Pro Lys His Phe Ala Glu Ala Lys Glu
    210                 215                 220

Phe Val Lys Gln Cys Ser Pro Ile Ile Arg Ala Asp Leu Asn Ile Val
225                 230                 235                 240

Arg Ser Cys Thr Ser Asn Val Pro Ser Lys Ala Val Leu Ser Cys Asp
                245                 250                 255

Leu Thr Cys Phe Val Gly Ser Glu Asp Ile Ala Lys Asp Met Glu Ala
            260                 265                 270

Trp Lys Asp Val Thr Ser Gly Asn Ala Lys Ile Tyr Gln Leu Pro Gly
        275                 280                 285

Gly His Phe Tyr Leu Leu Asp Pro Ala Asn Glu Lys Leu Ile Lys Asn
    290                 295                 300

Tyr Ile Ile Lys Cys Leu Glu Val Ser Ser Ile Ser Asn Phe
305                 310                 315
```

<210> SEQ ID NO 17
<211> LENGTH: 63
<212> TYPE: DNA
<213> ORGANISM: Homo sapiens

<400> SEQUENCE: 17

```
gatggaattc ccatggagca tcaccatcac catcacatgg agagaggaga ccaacctaag      60
aga                                                                   63

<210> SEQ ID NO 18
<211> LENGTH: 36
<212> TYPE: DNA
<213> ORGANISM: Homo sapiens

<400> SEQUENCE: 18
gatctcgagc taaaaattgg atatcgatga tacttc                               36
```